US00RE47047E

(19) United States
(12) Reissued Patent
Berger et al.

(10) Patent Number: US RE47,047 E
(45) Date of Reissued Patent: Sep. 18, 2018

(54) 5-[(3,3,3-TRIFLUORO-2-HYDROXY-1-ARYLPROPYL)AMINO]-1H-QUINOLIN-2-ONES, A PROCESS FOR THEIR PRODUCTION AND THEIR USE AS ANTI-INFLAMMATORY AGENTS

(71) Applicants: ASTRAZENECA AB, Sodertalje (SE); BAYER INTELLECTUAL PROPERTY GMBH, Monheim (DE)

(72) Inventors: Markus Berger, Berlin (DE); Hartmut Rehwinkel, Berlin (DE); Thomas Zollner, Berlin (DE); Ekkehard May, Berlin (DE); Jorma Hassfeld, Berlin (DE); Heike Schaecke, Berlin (DE)

(73) Assignees: ASTRAZENECA AB, Sodertalje (SE); BAYER INTELLECTUAL PROPERTY GMBH, Monheim (DE)

(21) Appl. No.: 15/080,187

(22) Filed: Mar. 24, 2016

Related U.S. Patent Documents

Reissue of:
(64) Patent No.: 8,680,117
Issued: Mar. 25, 2014
Appl. No.: 13/614,161
Filed: Sep. 13, 2012

U.S. Applications:
(62) Division of application No. 12/275,392, filed on Nov. 21, 2008, now Pat. No. 8,394,958.

(60) Provisional application No. 60/990,116, filed on Nov. 26, 2007.

(30) Foreign Application Priority Data

Nov. 22, 2007 (EP) ..... 07076019

(51) Int. Cl.

| | |
|---|---|
| ***A61K 31/04*** | (2006.01) |
| ***C07D 215/38*** | (2006.01) |
| ***C07C 45/00*** | (2006.01) |
| ***C07D 405/12*** | (2006.01) |
| ***C07C 45/58*** | (2006.01) |
| ***C07C 49/84*** | (2006.01) |
| ***C07C 45/71*** | (2006.01) |
| ***C07C 49/82*** | (2006.01) |
| ***C07D 303/32*** | (2006.01) |

(52) U.S. Cl.
CPC ..... *C07D 215/38* (2013.01); *C07C 45/00* (2013.01); *C07C 45/58* (2013.01); *C07C 45/71* (2013.01); *C07C 49/82* (2013.01); *C07C 49/84* (2013.01); *C07D 303/32* (2013.01); *C07D 405/12* (2013.01)

(58) Field of Classification Search
CPC .. C07D 215/38; C07D 303/32; C07D 405/12; C07C 45/58; C07C 45/71; C07C 49/82; C07C 49/84; C07C 45/00
See application file for complete search history.

(56) References Cited

U.S. PATENT DOCUMENTS

| | | | | |
|---|---|---|---|---|
| 3,485,842 | A | 12/1969 | Davoll | |
| 4,189,453 | A | 12/1980 | Lorenz et al. | |
| 7,129,270 | B2 | 10/2006 | JaRoch et al. | |
| 7,442,794 | B2 * | 10/2008 | Rehwinkel et al. | 544/235 |
| 7,999,108 | B2 * | 8/2011 | Berger et al. | 546/159 |
| 8,173,676 | B2 | 5/2012 | Berger et al. | |
| 2002/0077356 | A1 | 6/2002 | Jaroch et al. | |
| 2005/0009109 | A1 | 1/2005 | Moerner et al. | |
| 2005/0090559 | A1 | 4/2005 | Berger et al. | |
| 2005/0131226 | A1 | 6/2005 | Rehwinkel et al. | |
| 2006/0040933 | A1 | 2/2006 | Jaroch et al. | |
| 2006/0040993 | A1 | 2/2006 | Jaroch et al. | |
| 2010/0016338 | A1 | 1/2010 | Berger et al. | |

FOREIGN PATENT DOCUMENTS

| | | |
|---|---|---|
| GB | 1 045 180 | 10/1966 |
| JP | 6 172321 | 6/1994 |
| WO | 1997 14691 | 4/1997 |
| WO | 00 10977 | 3/2000 |
| WO | 2002 10143 | 2/2002 |
| WO | 2003 082787 | 10/2003 |

(Continued)

OTHER PUBLICATIONS

Cooper, Am. J. Respri. Cirt. Car. Med., Apr. 2001, vol. 163, No. 5, pp. 1198-1205.
Agiro Kanesho Co Ltd., "Substituted aminopyrididine derivative, its production and pest exterminating agent comprising the same as active ingredient," Patent Abstracts of Japan, Publication Date: Jun. 21, 1994; English Abstract of JP-6 172321.
Database Caplus Chemical Abstract Service, "5-[[[4-(dimethuylamino) phenyl] methylene] amino]-6-methoxy-4-methy7l," Aug. 16, 2005, XP002487276.
Leitner, Int. J. Immunopathol. Pharmacol, Jan.-Mar. 2007, vol. 20, No. 1, pp. 25-36.

(Continued)

*Primary Examiner* — Yong Chong
(74) *Attorney, Agent, or Firm* — Millen, White, Zelano and Branigan, P.C.

(57) ABSTRACT

The present invention relates to compounds of formula I, (I)

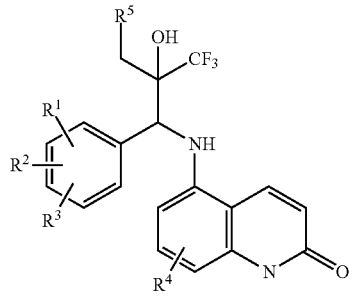

processes for their production and their use as anti-inflammatory agents.

22 Claims, No Drawings

(56) References Cited

FOREIGN PATENT DOCUMENTS

| | | |
|---|---|---|
| WO | 2005 035518 | 4/2005 |
| WO | 2005 003098 | 1/2006 |

OTHER PUBLICATIONS

Agro Kanesho Co Ltd., "Substituted aminopyrididine derivative, its production and pest exterminating agent comprising the same as active ingredient," Patent Abstracts of Japan, Publication Date: Jun. 21, 1994; English Abstract of JP-6 172321.
Annex to form PCT/ISA.206 for PCT/EP2008/009440, 2008.
Bartoli, G. et al., "Asymmetric aminolysis of aromatic epoxides: a facile catalytic enantioselective synthesis of anit-beta-aminoalcohols," Organic Letters, 2004, vol. 6, No. 13, pp. 2173-2176.
Besedovsky, Nature Immunology, 2006, vol. 7, pp. 537.
Cooper, Am. J. Respri. Cirt. Car. Med., Apr. 2001, vol. 163, No. 5, pp. 2173-2176.
Database Beilstein [Online] Beilstein Institute for Organic Chemistry, Aust. J. Chem., 1966, vol. 19, pp. 2389-2392, XP-002458022.
Database Beilstein [Online] Beilsten Institute for Organic Chemistry, Indian Journal of Chemistry, 1978, vol. 16, XP-002458021.
Demir, A. S. et al., "Generation of acylanion equivalents from acylphosphonates via phosphonate-phosphate rearrangement: a highly practical method for cross-benzoin reaction," Journal of Organic Chemistry, 2005, vol. 70, pp. 10584-10587.
Kohyama, Antimicrobial Agents and Chemotherapy, Apr. 1999, vol. 43, pp. 907-911.
Monti, L. et al., "Some quinoline compounds," Database Caplus Chemical Abstract Service, Dec. 16, 2001, XP002487275.
Takikawa, G. et al., "Preparation and Synthetic Application of a Novel Ketene Silyl Acetal of Methyl Trifluoropyruvate," Journal of Organic Chemistry, 2005, vol. 70, pp. 8811-8816.
Yamauchi, Y. et al., "Trifluoromethyl-stabilized optically active oxiranyl and aziridinyl anions for stereospecific syntheses of trifluoromethylated compounds," Tetrahedron, 2003, vol. 59, pp. 9839-9847.
Office Action for Japanese Patent Application No. 2009 51975 dated Sep. 24, 2012.
English Translation of Office Action for Japanese Patent Application No. 2009 51975 dated Sep. 24, 2012.

* cited by examiner

5-[(3,3,3-TRIFLUORO-2-HYDROXY-1-ARYLPROPYL)AMINO]-1H-QUINOLIN-2-ONES, A PROCESS FOR THEIR PRODUCTION AND THEIR USE AS ANTI-INFLAMMATORY AGENTS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application is a divisional application of U.S. Ser. No. 12/275,392, filed Nov. 21, 2008, now pending which claims the benefit of the filing date of U.S. Provisional Application Ser. No. 60/990,116, filed Nov. 26, 2007.

The present invention relates to compounds of formula I, a process for their production and their use as anti-inflammatory agents.

The most common anti-inflammatory agents are still the glucocorticoids (GCs) which are small molecules having a steroidal structure that interact with the glucocorticoid receptor (GR), whether endogenous, like cortisol, or synthetic, like dexamethasone and others. However, the application of highly potent GCs, especially over long treatment periods, led to the occurrence of undesired effects. A number of these effects, are severe and sometimes irreversible such as e.g. diabetes, osteoporosis, skin and muscle atrophy, glaucoma (Schäcke et al., 2002 Pharmacol. & Therapeutics (2002) 96(1):23-43, Miner et al., 2005 Expert Opin. Investig. Drugs (2005) 14(12):1527-1545.) The GCs potently inhibit pro-inflammatory cytokines and chemokines at the site of administration, whereas they elicit only limited systemic effects (O'Connell, 2003 Clin. Ther. (2003) 25(Suppl. C):C42-60; Welker et al. Int. Arch. Allergy Immunol. (1996) 109(2):110-115, 1996, Gunther et al., 1998. Skin Pharmacol. Appl. Skin Physiol. (1998) 11(1):35-42). Although locally active GCs appeared to be the ideal anti-inflammatory drugs, their application is limited due to local side effects and to insufficient efficacy in severe disease states.

Therefore, there is a great medical need for new compounds that have anti-inflammatory/immunomodulatory activity similar to the marketed GCs, and are less likely to produce undesired effects.

From the prior art of DE 100 38 639 and WO 02/10143, anti-inflammatory agents of the following general formula

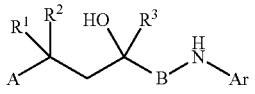

are known, wherein the Ar radical comprises phthalides, thiophthalides, benzoxazinones or phthalazinones. In the experiment, these compounds show dissociations of action between anti-inflammatory and undesirable metabolic actions and are superior to the previously described non-steroidal glucocorticoids or exhibit at least just as good an action.

Compounds structurally related to those described in this patent application are disclosed in WO 2005/035518.

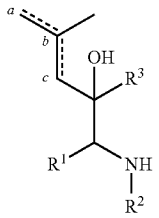

Due to the manufacturing process these compound always do contain a group

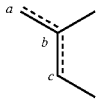

wherein the bond between a and b or between b and c may be unsaturated and which thus must contain a group selected from —$CH_2$—$CH(CH_3)_2$, a —CH═$C(CH_3)_2$ or a —$CH_2$—$C(CH_3)$═$CH_2$). Compounds of such a composition are specifically disclaimed in the present application.

Despite all efforts, the selectivity of the compounds of the prior art towards the glucocorticoid receptor (GR) compared to the other steroid receptors as well as their efficacy or potency still requires improvement.

It was therefore the object of this invention to make compounds available showing improvements of at least one aspect mentioned above.

This object has been achieved by the compounds according to the claims.

This invention therefore relates to compounds of general formula I (I)

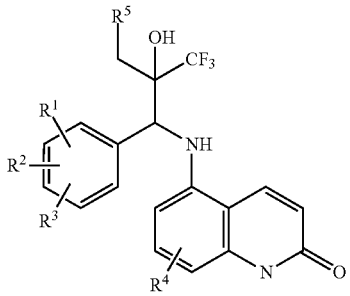

wherein $R^1$ and $R^2$ independently of one another, mean a hydrogen atom, a hydroxy group, a halogen atom, an optionally substituted ($C_1$-$C_{10}$)-alkyl group, an optionally substituted ($C_1$-$C_{10}$)-alkoxy group, a ($C_1$-$C_{10}$)-alkylthio group, a ($C_1$-$C_5$)-perfluoroalkyl group, a cyano group, a nitro group, or $R^1$ and $R^2$ together mean a group that is selected from the groups —O—$(CH_2)_p$—O—, —O—$(CH_2)_p$—$CH_2$—, —O—CH═CH—, —$(CH_2)_{p+2}$—, —NH—$(CH_2)_{p+1}$, —N($C_1$-$C_3$-alkyl)-$(CH_2)_{p+1}$, and —NH—N═CH—, whereby p=1 or 2, and the terminal oxygen atoms and/or carbon atoms and/or nitrogen atoms are linked to directly adjacent ring-carbon atoms, or $NR^6R^7$, whereby $R^6$ and $R^7$, independently of one another, mean hydrogen, $C_1$-$C_5$-alkyl or (CO)—($C_1$-$C_5$)-alkyl, $R^3$ means a hydrogen atom, a hydroxy group, a halogen atom, a cyano group, an optionally substituted ($C_1$-$C_{10}$)-alkyl group, a ($C_1$-$C_{10}$)-alkoxy group, a ($C_1$-$C_{10}$)-alkylthio group, or a ($C_1$-$C_5$)-perfluoroalkyl group, $R^4$ means a hydrogen, halogen, hydroxy, ($C_1$-$C_5$)-alkyl, ($C_1$-$C_5$)alkoxy, ($C_1$-$C_5$)-alkylthio, ($C_1$-$C_5$)-perfluoroalkyl, cyano, nitro, $NR^6R^7$, $COOR^9$, $(CO)NR^6R^7$ or a ($C_1$-$C_5$-alkylene)-O—(CO)—($C_1$-$C_5$)alkyl group $R^5$ means a group selected from —($C_1$-$C_{10}$)alkyl, which may be optionally partially or completely halogenated, —($C_2$-$C_{10}$)alkenyl, —($C_2$-$C_{10}$)alkynyl, ($C_3$-$C_7$)cycloalkyl-($C_1$-$C_8$)alkyl, ($C_3$-$C_7$)cycloalkyl-($C_1$-$C_8$)alkyenyl, ($C_3$-$C_7$)cycloalkyl-($C_2$-$C_8$)alkynyl, heterocyclyl-($C_1$-$C_8$)alkyl, heterocyclyl-($C_1$-$C_8$)alkenyl, heterocyclyl-($C_2$-$C_8$)alkynyl, $R^8$, $R^8$—($C_1$-$C_8$)alkyl, $R^8$—($C_2$-$C_8$)alkenyl, $R^8$—($C_2$-$C_8$)alkynyl, —S—($C_1$-$C_{10}$)-alkyl, —$SO_2$—($C_1$-$C_{10}$)-alkyl

—S—$R^8$,

—$SO_2$—$R^8$,

—CN

-Hal,

—O—($C_1$-$C_{10}$)-alkyl,

—$NR^6R^7$ wherein $R^6$, $R^7$ have the meaning defined above

—O—$R^8$,

—OH with the exception of —$CH(CH_3)_2$, or —$C(CH_3)$=$CH_2$ $R^8$ means an aryl group which may optionally be substituted by 1-3 hydroxy, halogen, $C_1$-$C_5$-alkyl, $C_1$-$C_5$-alkoxy, cyano, $CF_3$, nitro, COO($C_1$-$C_5$-alkyl) or C(O)$OCH_2$-phenyl or a heteroaryl group whereby the heteroaryl group may contain 1-3 hetero atoms which may optionally be substituted by 1-3 alkyl groups, hydroxy, halogen, cyano or $C_1$-$C_5$-alkoxy groups.

and their salts, solvates or salts of solvates.

One aspect of the invention relates to compounds of formula I wherein $R^1$ and $R^2$ independently of one another, mean a hydrogen atom, a hydroxy group, a halogen atom, an optionally substituted ($C_1$-$C_{10}$)-alkyl group, an optionally substituted ($C_1$-$C_{10}$)-alkoxy group, a ($C_1$-$C_{10}$)-alkylthio group, a ($C_1$-$C_5$)-perfluoroalkyl group, a cyano group, a nitro group, or $R^1$ and $R^2$ together mean a group that is selected from the groups —O—$(CH_2)_p$—O—, —O—$(CH_2)_p$—$CH_2$—, —O—CH=CH—, —$(CH_2)_{p+2}$—, —NH—$(CH_2)_{p+2}$—, —N($C_1$-$C_3$-alkyl)-$(CH_2)_{p+1}$, and —NH—N=CH—, whereby p=1 or 2, and the terminal oxygen atoms and/or carbon atoms and/or nitrogen atoms are linked to directly adjacent ring-carbon atoms, or $NR^6R^7$, whereby $R^6$ and $R^7$, independently of one another mean hydrogen, $C_1$-$C_5$-alkyl or (CO)—($C_1$-$C_5$)-alkyl, $R^3$ means a hydrogen atom, a hydroxy group, a halogen atom, a cyano group, an optionally substituted ($C_1$-$C_{10}$)-alkyl group, a ($C_1$-$C_{10}$)-alkoxy group, a ($C_1$-$C_{10}$)-alkylthio group, or a ($C_1$-$C_5$)-perfluoroalkyl group, $R^4$ means a hydrogen atom, a hydroxy group, a halogen atom, $R^5$ means a group selected from —($C_1$-$C_{10}$)alkyl, which may be optionally partially or completely halogenated —($C_2$-$C_{10}$)alkenyl, —($C_2$-$C_{10}$)alkynyl, ($C_3$-$C_7$)cycloalkyl-($C_1$-$C_8$)alkyl, ($C_3$-$C_7$)cycloalkyl-($C_2$-$C_8$)alkenyl, ($C_3$-$C_7$)cycloalkyl-($C_2$-$C_8$)alkynyl, heterocyclyl-($C_1$-$C_8$)alkyl, heterocyclyl-($C_2$-$C_8$)alkenyl, heterocyclyl-($C_2$-$C_8$)alkynyl,

—$R^8$, $R^8$—($C_1$-$C_8$)alkyl, $R^8$—($C_2$-$C_8$)alkenyl, $R^8$—($C_2$-$C_8$)alkynyl, —S—($C_1$-$C_{10}$)-alkyl,

—S—$R^8$,

—$SO_2$—$R^8$,

—$SO_2$—($C_1$-$C_{10}$)-alkyl,

—CN,

-Hal,

—O—($C_1$-$C_{10}$)-alkyl,

—$NR^6R^7$ wherein $R^6$, $R^7$ have the meaning indicated above

—O—$R^8$,

—OH with the exception of —$CH(CH_3)_2$, or —$C(CH_3)$=$CH_2$ $R^8$ means an aryl which may optionally be substituted with 1-3 alkyl, hydroxy, halogen, cyano or $C_1$-$C_5$-alkoxy-groups or a heteroarylgroup wherein the heteroarylgroup may contain 1-3 heteroatoms which may optionally be substituted with 1-3 alkyl, hydroxy, halogen, cyano or $C_1$-$C_5$-alkoxygroups, n means an integer selected from 1, 2, 3, 4, 5 and their salts, solvates or salts of solvates.

Another aspect of the invention are compounds of general formula I according to claim 1, wherein $R^1$ and $R^2$ independently of one another, mean a hydrogen atom, a hydroxyl group, a halogen atom, an optionally substituted ($C_1$-$C_{10}$)-alkyl group, an optionally substituted ($C_1$-$C_{10}$)-alkoxy group, a ($C_1$-$C_5$)-perfluoroalkyl group, a cyano group, or $NR^6R^7$, whereby $R^6$ and $R^7$, independently of one another, mean hydrogen, $C_1$-$C_5$-alkyl or (CO)—($C_1$-$C_5$)-alkyl, $R^3$ means a hydrogen atom, a hydroxy group, a halogen atom, a cyano group, an optionally substituted ($C_1$-$C_{10}$)-alkyl group, a ($C_1$-$C_{10}$)-alkoxy group, or a ($C_1$-$C_5$)-perfluoroalkyl group, $R^4$ means hydrogen, $C_1$-$C_3$-alkyl, $C_1$-$C_3$-alkoxy, hydroxy, halogen, $R^5$ means a group selected from —($C_1$-$C_{10}$)-alkyl, which may be optionally partially or completely halogenated —($C_2$-$C_{10}$)-alkenyl, —($C_2$-$C_{10}$)-alkynyl, —($C_3$-$C_7$)cycloalkyl-($C_1$-$C_8$)alkyl, —($C_3$-$C_7$)cycloalkyl-($C_2$-$C_8$)alkenyl, —S—($C_1$-$C_{10}$)-alkyl, —$SO_2$—($C_1$-$C_{10}$)-alkyl, —CN, -Hal, —O—($C_1$-$C_{10}$)-alkyl, —$NR^6R^7$ wherein $R^6$, $R^7$ have the meaning defined above, —OH with the exception of —$CH(CH_3)_2$, or —$C(CH_3)$=$CH_2$ and their salts, solvates or salts of solvates. A further aspect of the invention are compounds of general formula I according to claim 1, wherein $R^1$, $R^2$ and $R^3$ are independently of one another hydrogen, fluorine, chlorine, bromine, a cyano group, a methoxy group, a ethoxy group, a hydroxy group, $R^4$ is hydrogen, $C_1$-$C_3$-alkyl, halogen, $R^5$ is hydroxyl group, chlorine, —S—$CH_3$, —S—$CH_2$—$CH_3$, —S—$CH_2$—$CH_2$—$CH_3$, —O—$CH_3$ or —O—$CH_2$—$CH_3$, —O—$CH_2$—$CH_2$—$CH_3$, —N—$(CH_3)_2$, —N—$(CH_2$—$CH_3)_2$ and their salts, solvates or salts of solvates. A further aspect of the invention are compounds of general formula I according to claim 1, wherein $R^1$, $R^2$ and $R^3$ are independently of one another hydrogen, fluorine, chlorine, bromine, a cyano group, a methoxy group, a ethoxy group, a hydroxyl group, $R^4$ is hydrogen, $C_1$-$C_3$-alkyl, halogen, $R^5$ is a hydroxyl group, chlorine, —S—$CH_3$, —S—$CH_2$—$CH_3$, —S—$CH_2$—$CH_2$—$CH_3$, —O—$CH_3$, —O—$CH_2$—$CH_3$, —O—$CH_2$—$CH_2$—$CH_3$ or $N(CH_3)_2$ and their salts, solvates or salts of solvates.

Still another aspect of the invention are compounds of general formula I according to claim 1, wherein $R^1$, $R^2$ and $R^3$ are independently of one another hydrogen, fluorine, chlorine, bromine, a cyano group, a methoxy group, a ethoxy group, a hydroxyl group, $R^4$ is hydrogen, $C_1$-$C_3$-alkyl, halogen, $R^5$ is a hydroxyl group, chlorine, —S—$CH_3$, —S—$CH_2$—$CH_3$, —S—$CH_2$—$CH_2$—$CH_3$, —O—$CH_3$ or —O—$CH_2$—$CH_3$, —O—$CH_2$—$CH_2$—$CH_3$ and their salts, solvates or salts of solvates.

One aspect of the invention are compounds of general formula I according to claim 1, wherein $R^1$ and $R^2$ are independently of one another hydrogen, fluorine, chlorine, a methoxy group, a hydroxyl group, $R^3$ is hydrogen, fluorine, chlorine or a methoxy group, $R^4$ is hydrogen or fluorine, $R^5$ is a hydroxy group, a chlorine atom, —S—$CH_3$, —S—$CH_2$—$CH_3$, —O—$CH_3$, —O—$CH_2$—$CH_3$ or $N(CH_3)_2$ and their salts, solvates or salts of solvates. A further aspect of the invention are compounds of general formula I according to claim 1, wherein $R^1$ and $R^2$ are independently of one another hydrogen, fluorine, chlorine, a methoxy group, $R^3$ is hydrogen, fluorine, chlorine or a methoxy group, $R^4$ is hydrogen or fluorine, $R^5$ is a hydroxyl group, a chlorine atom, —S—$CH_3$, —S—$CH_2$—$CH_3$, —O—$CH_3$, or —O—$CH_2$—$CH_3$ and their salts, solvates or salts of solvates.

Another aspect of the invention are compounds according to at least one of claims 1-4 in enantiomerically pure form and their salts, solvates or salts of solvates. Another aspect of the invention are compounds according to claim 1 selected from the list consisting of 5-{[1-(2-Fluoro-4-methoxyphenyl)-3,3,3-trifluoro-2-hydroxy-2-([methylsulfanyl]methyl)propyl]amino}-1H-quinolin-2-one 5-{[2-([Ethylsulfanyl]methyl)-1-(2-fluoro-4-methoxyphenyl)-3,3,3-trifluoro-2-hydroxypropyl]amino}-1H-quinolin-2-one 5-{[1-(2-Chloro-3-fluoro-4-methoxyphenyl)-3,3,3-trifluoro-2-hydroxy-2-([methylsulfanyl]methyl)propyl]amino}-1H-quinolin-2-one 5-{[1-(2-Chloro-3-fluoro-4-methoxyphenyl)-2-([ethylsulfanyl]methyl)-3,3,3-trifluoro-2-hydroxypropyl]amino}-7-fluoro-1H-quinolin-2-one 5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one 5-{[1-(2-Chloro-3-fluoro-4-methoxyphenyl)-2-(ethoxymethyl)-3,3,3-trifluoro-2-hydroxypropyl]amino}-7-fluoro-1H-quinolin-2-one 5-{[1-(2-Chloro-3-fluoro-4-methoxyphenyl)-3,3,3-trifluoro-2-hydroxy-2-(hydroxymethyl)propyl]amino}-7-fluoro-1H-quinolin-2-one 5-{[1-(5-Chloro-3-fluoro-2-methoxyphenyl)-3,3,3-trifluoro-2-hydroxy-2-(hydroxymethyl)-propyl]amino}-7-fluoro-1H-quinolin-2-one 5-{[1-(5-Chloro-3-fluoro-2-methoxyphenyl)-2-(chloromethyl)-3,3,3-trifluoro-2-hydroxypropyl]amino}-7-fluoro-1H-quinolin-2-one 5-{[3,3,3-trifluoro-2-hydroxy-2-([methoxymethyl)-1-phenylpropyl]amino}-1H-quinolin-1-one 5-{[1-(2-Chloro-3-fluoro-4-methoxyphenyl)-2-(diaminomethyl)-3,3,3-trifluoro-2-hydroxypropyl]amino}-7-fluoro-1H-quinolin-2-one 5-{[1-(4-Chloro-3-fluoro-2-methoxyphenyl)-3,3,3-trifluoro-2-hydroxy-2-(methoxymethyl)propyl]amino}-7-fluoro-1H-quinolin-2-one 5-{[1-(2-Chloro-3-fluoro-4-methoxyphenyl)-2-(ethoxymethyl)-3,3,3-trifluoro-2-hydroxypropyl]amino}-7-fluoro-1H-quinolin-2-one 5-{[1-(2-Chloro-3-fluoro-4-hydroxyphenyl)-3,3,3-trifluoro-2-hydroxy-2-(hydroxymethyl)propyl]amino}-7-fluoro-1H-quinolin-2-one and their salts, solvates or salts of solvates.

Still another aspect of the invention are enantiomerically pure compounds according to claim 1 selected from the list consisting of 5-{[1-(2-Fluoro-4-methoxyphenyl)-3,3,3-trifluoro-2-hydroxy-2-([methylsulfanyl]methyl)propyl]amino}-1H-quinolin-2-one 5-{[2-([Ethylsulfanyl]methyl)-1-(2-fluoro-4-methoxyphenyl)-3,3,3-trifluoro-2-hydroxypropyl]amino}-1H-quinolin-2-one 5-{[1-(2-Chloro-3-fluoro-4-methoxyphenyl)-3,3,3-trifluoro-2-hydroxy-2-([methylsulfanyl]methyl)propyl]amino}-1H-quinolin-2-one 5-{[1-(2-Chloro-3-fluoro-4-methoxyphenyl)-2-([ethylsulfanyl]methyl)-3,3,3-trifluoro-2-hydroxypropyl]amino}-7-fluoro-1H-quinolin-2-one 5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one 5-{[1-(2-Chloro-3-fluoro-4-methoxyphenyl)-2-(ethoxymethyl)-3,3,3-trifluoro-2-hydroxypropyl]amino}-7-fluoro-1H-quinolin-2-one 5-{[1-(2-Chloro-3-fluoro-4-methoxyphenyl)-3,3,3-trifluoro-2-hydroxy-2-(hydroxymethyl)propyl]amino}-7-fluoro-1H-quinolin-2-one 5-{[1-(5-Chloro-3-fluoro-2-methoxyphenyl)-3,3,3-trifluoro-2-hydroxy-2-(hydroxymethyl)-propyl]amino}-7-fluoro-1H-quinolin-2-one 5-{[1-(5-Chloro-3-fluoro-2-methoxyphenyl)-2-(chloromethyl)-3,3,3-trifluoro-2-hydroxypropyl]amino}-7-fluoro-1H-quinolin-2-one 5-{[3,3,3-trifluoro-2-hydroxy-2-([methoxymethyl)-1-phenylpropyl]amino}-1H-quinolin-1-one and their salts, solvates or salts of solvates.

Another aspect of the invention are enantiomerically pure compounds according to claim 1 selected from the list consisting of 5-{(1S,2R)[1-(2-Fluoro-4-methoxyphenyl)-3,3,3-trifluoro-2-hydroxy-2-([methylsulfanyl]methyl)propyl]amino}-1H-quinolin-2-one 5-{(1S,2R)[1-(2-([Ethylsulfanyl]methyl)-1-(2-fluoro-4-methoxyphenyl)-3,3,3-trifluoro-2-hydroxypropyl]amino}-1H-quinolin-2-one 5-{(1S,2R)[1-(2-Chloro-3-fluoro-4-methoxyphenyl)-3,3,3-trifluoro-2-hydroxy-2-([methylsulfanyl]methyl)propyl]amino}-1H-quinolin-2-one 5-{(1S,2R)[1-(2-Chloro-3-fluoro-4-methoxyphenyl)-2-([ethylsulfanyl]methyl)-3,3,3-trifluoro-2-hydroxypropyl]amino}-7-fluoro-1H-quinolin-2-one 5-{(1S,2S)[1-(2-Chloro-3-fluoro-4-methoxyphenyl)-3,3,3-trifluoro-2-hydroxy-2-(methoxymethyl)propyl]amino}-7-fluoro-1H-quinolin-2-one 5-{(1S,2S)[1-(2-Chloro-3-fluoro-4-methoxyphenyl)-2-(ethoxymethyl)-3,3,3-trifluoro-2-hydroxypropyl]amino}-7-fluoro-1H-quinolin-2-one 5-{(1S,2S)[1-(2-Chloro-3-fluoro-4-methoxyphenyl)-3,3,3-trifluoro-2-hydroxy-2-(hydroxymethyl)propyl]amino}-7-fluoro-1H-quinolin-2-one 5-{(1S,2S)[1-(5-Chloro-3-fluoro-2-methoxyphenyl)-3,3,3-trifluoro-2-hydroxy-2-(hydroxymethyl)propyl]amino}-7-fluoro-1H-quinolin-2-one 5-{(1S,2R)[1-(5-Chloro-3-fluoro-2-methoxyphenyl)-2-(chloromethyl)-3,3,3-trifluoro-2-hydroxypropyl]amino}-7-fluoro-1H-quinolin-2-one 5-{(1S,2S)[3,3,3-trifluoro-2-hydroxy-2-([methoxymethyl)-1-phenylpropyl]amino}-1H-quinolin-1-one 5-{[(1S,2R)[1-(2-Chloro-3-fluoro-4-methoxyphenyl)-2-(diaminomethyl)-3,3,3-trifluoro-2-hydroxypropyl]amino}-7-fluoro-1H-quinolin-2-one 5-{(1S,2S)[1-(2-Chloro-3-fluoro-4-hydroxyphenyl)-3,3,3-trifluoro-2-hydroxy-2-(hydroxymethyl)propyl]amino}-7-fluoro-1H-quinolin-2-one and their salts, solvates or salts of solvates.

A further aspect of the invention are enantiomerically pure compounds according to claim 1 selected from the list consisting of 5-{(1S,2R)[1-(2-Fluoro-4-methoxyphenyl)-3,3,3-trifluoro-2-hydroxy-2-[([methylsulfanyl]methyl)propyl]amino}-1H-quinolin-2-one 5-{(1S,2R)[2-([Ethylsulfanyl]methyl)-1-(2-fluoro-4-methoxyphenyl)-3,3,3-trifluoro-2-hydroxypropyl]amino}-1H-quinolin-2-one 5-{(1S,2R)[1-(2-Chloro-3-fluoro-4-methoxyphenyl)-3,3,3-trifluoro-2-hydroxy-2-([methylsulfanyl]methyl)propyl]amino}-1H-quinolin-2-one 5-{(1S,2R)[1-(2-Chloro-3-fluoro-4-methoxyphenyl)-2-([ethylsulfanyl]methyl)-3,3,3-trifluoro-2-hydroxypropyl]amino}-7-fluoro-1H-quinolin-2-one 5-{(1S,2S)[1-(2-Chloro-3-fluoro-4-methoxyphenyl)-3,3,3-trifluoro-2-hydroxy-2-(methoxymethyl)propyl]amino}-7-fluoro-1H-quinolin-2-one 5-{(1S,2S)[1-(2-Chloro-3-fluoro-4-methoxyphenyl)-2-(ethoxymethyl)-3,3,3-trifluoro-2-hydroxypropyl]amino}-7-fluoro-1H-quinolin-2-one 5-{(1S,2S)[1-(2-Chloro-3-fluoro-4-methoxyphenyl)-3,3,3-trifluoro-2-hydroxy-2-(hydroxymethyl)propyl]amino}-7-fluoro-1H-quinolin-2-one 5-{(1S,2S)[1-(5-Chloro-3-fluoro-2-methoxyphenyl)-3,3,3-trifluoro-2-hydroxy-2-(hydroxymethyl)propyl]amino}-7-fluoro-1H-quinolin-2-one 5-{(1S,2R)[1-(5-Chloro-3-fluoro-2-methoxyphenyl)-2-(chloromethyl)-3,3,3-trifluoro-2-hydroxypropyl]amino}-7-fluoro-1H-quinolin-2-one 5-{(1S,2S)[3,3,3-trifluoro-2-hydroxy-2-([methoxymethyl)-1-phenylpropyl]amino}-1H-quinolin-1-one and their salts, solvates or salts of solvates.

Compounds of general formula I, wherein at least one of $R^1$, $R^2$ or $R^3$ are different from hydrogen are one preferred embodiment of the invention.

Compounds of general formula I according to claims 1-7, wherein at least one of $R^1$, $R^2$ or $R^3$ is different from hydrogen are one preferred embodiment of the invention.

In another embodiment two of $R^1$, $R^2$ or $R^3$ according to claim 1 or claims 1-7 are different from hydrogen.

In yet a further embodiment all three $R^1$, $R^2$ or $R^3$ according to claim 1 or claims 1-7 are different from hydrogen.

In one aspect of the invention the alkyl groups of the compounds of formula (I) have 1-5 carbon atoms.

In another aspect the alkyl groups of the compounds of formula (I) have 1-3 carbon atoms.

The quinolon ring of formula I can be substituted by a radical $R^4$ selected from the group consisting of halogen, hydroxy, $(C_1\text{-}C_5)$-alkyl, $(C_1\text{-}C_5)$alkoxy, $(C_1\text{-}C_5)$-alkylthio, $(C_1\text{-}C_5)$-perfluoroalkyl, cyano, nitro, $NR^7R^5COOR^9(CO)NR^7R^5$ or a $(C_1\text{-}C_5\text{-alkylene})\text{-O—(CO)—}(C_1\text{-}C_5)$alkyl group, preferably $R^4$ is selected from the group $C_1\text{-}C_3$-alkyl, $C_1\text{-}C_3$-alkoxy, hydroxy, halogen. In another aspect of the invention $R^4$ is selected from the group hydrogen, $C_1\text{-}C_3$-alkyl, halogen, hydroxy, preferably from hydrogen or halogen, more preferably from hydrogen, chlorine or fluorine.

Another subject of the invention are compounds according to formula I wherein $R^4$ is hydrogen or fluorine.

Yet another subject of the invention are compounds according to formula I wherein $R^4$ is fluorine.

More particularly compounds according to formula I wherein $R^4$ is a 7-fluoro-substituent or hydrogen and at least one of $R^1$, $R^2$ and $R^3$ is selected from chlorine, fluorine, methoxy, hydroxy, $R^5$ is selected from $S—CH_2—CH_3$, $—O—CH_2—CH_3$, $—S—CH_3$, $—O—CH_3—$, $N(CH_3)_2$, —OH and —Cl.

Another aspect of the invention are compounds according to formula I wherein $R^4$ is a 7-fluoro-substituent or hydrogen and at least one of $R^1$, $R^2$ and $R^3$ is selected from chlorine, fluorine, methoxy, $R^5$ is selected from $S—CH_2—CH_3$, $—O—CH_2—CH_3$, $—S—CH_3$, $—O—CH_3—$, —OH and —Cl. A preferred aspect of the invention are the subcombinations of all the residues as disclosed in the examples.

One aspect of the invention are compounds of general formula I, wherein the phenyl group is substituted with 1-3 of the same or different substituents $R^1$, $R^2$ and $R^3$. $R^1$ and $R^2$ are independently of one another, mean a hydrogen atom, a hydroxy group, a halogen atom, an optionally substituted $(C_1\text{-}C_{10})$-alkyl group, an optionally substituted $(C_1\text{-}C_{10})$-alkoxy group, a $(C_1\text{-}C_{10})$-alkylthio group, a $(C_1\text{-}C_5)$-perfluoroalkyl group, a cyano group, a nitro group, or $R^1$ and $R^2$ together mean a group that is selected from the groups $—O—(CH_2)_p—O—$, $—O—(CH_2)_p—CH_2—$, $—O—CH=CH—$, $—(CH_2)_{p+2}—$, $—NH—(CH_2)_{p+}$, $—N(C_1\text{-}C_3\text{-alkyl})\text{-}(CH_2)_{p+1}$, and $—NH—N=CH—$, whereby p=1 or 2, and the terminal oxygen atoms and/or carbon atoms and/or nitrogen atoms are linked to directly adjacent ring-carbon atoms, or $R^1$ and $R^2$ are $NR^6R^7$, whereby $R^6$ and $R^7$, independently of one another, mean hydrogen, $C_1\text{-}C_5$-alkyl or $(CO)—(C_1\text{-}C_5)$-alkyl. The third substituent $R^3$ means a hydrogen atom, a hydroxy group, a halogen atom, a cyano group, an optionally substituted $(C_1\text{-}C_{10})$-alkyl group, a $(C_1\text{-}C_{10})$-alkoxy group, a $(C_1\text{-}C_{10})$-alkylthio group, or a $(C_1\text{-}C_5)$-perfluoroalkyl group.

In another aspect any other phenyl group may be substituted by a group selected from $C_1\text{-}C_3$-alkoxy, hydroxy, and halogen, in particular methoxy, hydroxy, fluorine, chlorine, or bromine.

In another aspect of the invention $R^5$ of compounds of claim 1-6 selected from $—(C_1\text{-}C_{10})$-alkyl, which may be optionally partially or completely halogenated, $—(C_2\text{-}C_{10})$-alkenyl, $—(C_2\text{-}C_{10})$-alkynyl, $(C_3\text{-}C_7)$cycloalkyl-$(C_1\text{-}C_8)$alkyl, $(C_3\text{-}C_7)$cycloalkyl-$(C_2\text{-}C_8)$alkenyl, $(C_3\text{-}C_7)$cycloalkyl-$(C_1\text{-}C_8)$alkynyl, heterocyclyl-$(C_1\text{-}C_8)$alkyl, heterocyclyl-$(C_2\text{-}C_8)$alkenyl, heterocyclyl-$(C_2\text{-}C_8)$alkynyl —$R^8$, $R^8$—($C_1$-$C_8$)alkyl, $R^8$—($C_2$-$C_8$)alkenyl, $R^8$—($C_2$-$C_8$)alkynyl, —S—($C_1$-$C_{10}$)alkyl, —$SO_2$—($C_1$-$C_{10}$)alkyl-S—$R^5$, —$SO_2$—$R^5$, —CN, -Hal, —O—($C_1$-$C_{10}$)alkyl, —$NR^6R^7$ (wherein $R^6$, $R^7$ have the meaning defined above), —O—$R^8$ and —OH with the exception of —$CH(CH_3)_2$, or —$C(CH_3)$=$CH_2$. In yet another aspect $R^5$ is selected from the group consisting of —($C_1$-$C_{10}$)-alkyl, which may be optionally partially or completely halogenated, —($C_2$-$C_{10}$)-alkenyl, —($C_2$-$C_{10}$)-alkynyl, ($C_3$-$C_7$)cycloalkyl-($C_1$-$C_8$)alkyl, —($C_3$-$C_7$)cycloalkyl-($C_2$-$C_8$)alkenyl, —S—($C_1$-$C_{10}$)-alkyl, —$SO_2$—($C_1$-$C_{10}$)-alkyl, —CN, -Hal, —O—($C_1$-$C_{10}$)-alkyl, —$NR^6R^7$ (wherein $R^6$, $R^7$ have the meaning defined above), —OH with the exception of —$CH(CH_3)_2$, or —$C(CH_3)$=$CH_2$, preferably $R^5$ is —OH, Cl, —S—$CH_3$, —S—$CH_2$—$CH_3$, —S—$CH_2$—$CH_2$—$CH_3$, —O—$CH_3$, —O—$CH_2$—$CH_3$, —O—$CH_2$—$CH_2$—$CH_3$, $N(CH_3)_2$, $NHCH_3$ with the exception of —$CH(CH_3)_2$, or —$C(CH_3)$=$CH_2$, $R^5$ is most preferably is —OH, —S—$CH_3$, —S—$CH_2$—$CH_3$, —O—$CH_3$, —O—$CH_2$—$CH_3$ or $N(CH_3)_2$.

In another aspect of the invention $R^5$ of compounds of claim 1-6 selected from ($C_3$-$C_7$)cycloalkyl-($C_1$-$C_8$)alkyl, ($C_3$-$C_7$)cycloalkyl-($C_2$-$C_8$)alkenyl, ($C_3$-$C_7$)cycloalkyl-($C_1$-$C_8$)alkynyl, heterocyclyl-($C_1$-$C_8$)alkyl, heterocyclyl-($C_2$-$C_8$)alkenyl, heterocyclyl-($C_2$-$C_8$)alkynyl —$R^8$, —$R^8$—($C_1$-$C_8$)alkyl, $R^8$—($C_2$-$C_8$)alkenyl, $R^8$—($C_2$-$C_8$)alkynyl, —S—($C_1$-$C_{10}$)alkyl, —$SO_2$—($C_1$-$C_{10}$)alkyl-S—$R^8$, —$SO_2$—$R^8$, —CN, -Hal, —O—($C_1$-$C_{10}$)alkyl, —$NR^6R'$ (wherein $R^6$, $R^7$ have the meaning defined above), —O—$R^8$ and —OH.

In yet another aspect $R^5$ of compounds of claim 1-6 is selected from the group consisting of —($C_3$-$C_7$)cycloalkyl-($C_1$-$C_8$)alkyl, —($C_3$-$C_7$)cycloalkyl-($C_2$-$C_8$)alkenyl, —S—($C_1$-$C_{10}$)-alkyl, —$SO_2$—($C_1$-$C_{10}$)-alkyl, —CN, -Hal, —O—($C_1$-$C_{10}$)-alkyl, —$NR^6R^7$ (wherein $R^6$, $R^7$ have the meaning defined above), —OH; preferably $R^5$ is —OH, Cl, —S—$CH_3$, —S—$CH_2$—$CH_3$, —S—$CH_2$—$CH_2$—$CH_3$, —O—$CH_3$, —O—$CH_2$—$CH_3$, —O—$CH_2$—$CH_2$—$CH_3$, $N(CH_3)_2$, $NHCH_3$, $R^5$ is most preferably is —OH, —S—$CH_3$, —S—$CH_2$—$CH_3$, —O—$CH_3$, —O—$CH_2$—$CH_3$ or $N(CH_3)_2$.

Another aspect of the invention relates to compounds according to claims 1-6 wherein $R^5$ selected from —$R^8$, —S—($C_1$-$C_{10}$)-alkyl, —$SO_2$—($C_1$-$C_{10}$)-alkyl, —S—$R^8$, —$SO_2$—$R^8$, —CN, -Hal, —O—($C_1$-$C_{10}$)-alkyl, —$NR^6R^7$, wherein $R^6$, $R^7$ have the meaning defined in claim 1, —O—$R^8$ or —OH.

Another aspect of the invention relates to compounds according to claims 1-6 wherein $R^5$ selected from —S—($C_1$-$C_{10}$)-alkyl, —$SO_2$—($C_1$-$C_{10}$)-alkyl, —CN, -Hal, —O—($C_1$-$C_{10}$)-alkyl, —$NR^6R^7$, wherein $R^6$, $R^7$ have the meaning defined in claim 1, or —OH.

Another aspect of the invention relates to compounds according to claims 1-6 wherein $R^5$ selected from —S—($C_1$-$C_{10}$)-alkyl, —O—($C_1$-$C_{10}$)-alkyl, —$NR^6R^7$, wherein $R^6$, $R^7$ have the meaning defined in claim 1, or —OH.

One aspect of the invention are compounds according to claims 1-7, wherein $R^5$ is not —($C_1$-$C_{10}$)-alkyl or —($C_2$-$C_{10}$)-alkenyl.

Another aspect of the present invention are compounds of general formula I according to claims 1-7, wherein $R^5$ is not —($C_1$-$C_{10}$)-alkyl or —($C_2$-$C_{10}$)-alkenyl and from $R^1/R^2/R^3$ at least two are different from hydrogen or $R^1/R^2/R^3$ all are different from hydrogen and $R^4$ is halogen. In addition, the invention relates to the use of the compounds of general formula I for the production of pharmaceutical agents as well as their use for the production of pharmaceutical agents for treating inflammatory diseases.

DEFINITIONS

Unless otherwise notified the term "alkyl" refers to a straight or branched, substituted or unsubstituted chain. For example, the term propyl comprises $^{n}$-propyl and $^{iso}$-propyl, the term butyl comprises $^{n}$-butyl, $^{iso}$-butyl and $^{tert}$-butyl.

The alkyl groups can be straight-chain or branched and stand e.g. for a methyl, ethyl, n-propyl, iso-propyl, n-butyl, iso-butyl, tert-butyl or n-pentyl group, or a 2,2-dimethylpropyl, 2-methylbutyl or 3-methylbutyl group. A methyl or ethyl group is preferred. They can optionally be substituted by 1-3 hydroxy groups, cyano groups, halogen, 1-3 $C_1$-$C_5$-alkoxy groups, and/or 1-3 COO($C_1$-$C_{10}$-alkyl or benzyl) groups. Preferred are hydroxy groups. The total number of substituents depends on the number of carbon atoms of the chain. Usually the number of substituents does not exceed the number of carbon atoms except for halogen which leads at a maximum number of substituents to e.g. perfluorated alkyl groups.

For a partially or completely fluorinated $C_1$-$C_3$-alkyl group, the following partially or completely fluorinated groups are considered: fluoromethyl, difluoromethyl, trifluoromethyl, fluoroethyl, 1,1-difluoroethyl, 1,2-difluoroethyl, 1,1,1-trifluoroethyl, tetrafluoroethyl, and pentafluoroethyl. Of the latter, the trifluoromethyl group or the pentafluoroethyl group is preferred.

The $C_1$-$C_5$-alkoxy groups in $R^1$, $R^2$, $R^3$ and $R^5$ can be straight-chain or branched and stand for a methoxy, ethoxy, n-propoxy, iso-propoxy, n-butoxy, iso-butoxy, tert-butoxy or n-pentoxy, 2,2-dimethylpropoxy, 2-methylbutoxy or 3-methylbutoxy group. A methoxy or ethoxy group is preferred. They can optionally be substituted by $C_1$-$C_5$-alkyl groups, cyano groups or halogen The $C_1$-$C_5$-alkylthio groups can be straight-chain or branched and stand for a methylthio, ethylthio, n-propylthio, iso-propylthio, n-butylthio, iso-butylthio, tert-butylthio or n-pentylthio, 2,2-dimethylpropylthio, 2-methylbutylthio or 3-methylbutylthio group. A methylthio or ethylthio group is preferred.

The term halogen atom, Hal or halogen means a fluorine, chlorine, bromine or iodine atom. Preferred is a fluorine, chlorine or bromine atom.

The $NR^6R^7$ group includes, for example, $NH_2$, $N(H)CH_3$, $N(CH_3)_2$, $N(H)(CO)CH_3$, $N(CH_3)(CO)CH_3$, $N[(CO)CH_3]_2$, $N(H)CO_2CH_3$, $N(CH_3)CO_2CH_3$, or $N(CO_2CH_3)_2$.

The term $C_2$-$C_8$-alkenyl is a straight or branched, substituted or unsubstituted, chain including isomers having an E- or Z-configurated double bond such as e.g. vinyl, propen-1-yl, propen-2-yl (Allyl), but-1-en-1-yl, but-1-en-2-yl, but-2-en-1-yl, but-2-en-2-yl, 2-methyl-prop-2-en-1-yl, 2-methyl-prop-1-en-1-yl, but-1-en-3-yl, but-3-en-1-yl. If the alkenyl residue is placed between two other moieties the term alkenyl means alkenylene such as e.g. vinylene, propen-1-ylene, propen-2-ylene (Allylen), but-1-en-1-ylene, but-1-en-2-ylene, but-2-en-1-ylene, but-2-en-2-ylene, 2-methyl-prop-2-en-1-ylene, 2-methyl-prop-1-en-1-ylene, but-1-en-3-ylen, but-3-en-1-ylene.

The term $C_2$-$C_8$-alkynyl stands for a straight or branched chain e,g, —C≡CH, —$CH_2$—C≡CH, —C≡C—$CH_3$, —CH($CH_3$)—C≡CH, —C≡C—$CH_2$($CH_3$), —C($CH_3$)$_2$—C≡CH, —C≡C—CH($CH_3$)$_2$, —CH($CH_3$)—C≡C—$CH_3$, —$CH_2$—C≡C—$CH_2$($CH_3$) or, if the alkynyl residue is placed between two other moieties the term alkynyl means alkynylene such as e.g. —C≡C—, —$CH_2$—C≡C—, —C≡C—$CH_2$—, —CH($CH_3$)—C≡C—, —C≡C—CH($CH_3$)—, —C($CH_3$)$_2$—C≡C—, —C≡C—C—($CH_3$)$_2$—, —CH($CH_3$)—C≡C—$CH_2$—, —$CH_2$—C≡C—CH($CH_3$)—.

The term $C_3$-$C_7$-cycloalkyl means a substituted or unsubstituted group selected from cyclopropyl, cyclobutyl, cyclopentyl, cyclohexyl, cycloheptyl. The possible substitutents may be selected from hydroxy, halogen, $(C_1-C_5)$-alkyl, $(C_1-C_5)$-alkoxy, $NR^4R^8$, $COO(C_1-C_6)$-alkyl, CHO, cyano.

The term $C_3-C_7$-cycloalkyl-$(C_1-C_{10})$-alkyl- means e.g. —$(CH_2)$-cycloalkyl, —$(C_2H_4)$-cycloalkyl, —$(C_3H_6)$-cycloalkyl, —$(C_4H_8)$-cycloalkyl, —$(C_6H_{10})$-cycloalkyl whereby the cycloylkyl stand for e.g. cyclopropyl, cyclobutyl, cyclopentyl, cyclohexyl, cycloheptyl.

The term $C_3-C_7$-cycloalkyl-$(C_2-C_8)$-alkenyl means e.g. —(CH═CH)-cycloalkyl, —$[C(CH_3)═CH]$-cycloalkyl, —$[CH═C(CH_3)]$-cycloalkyl, —$(CH═CH—CH_2)$-cycloalkyl, —$(CH_2—CH═CH)$-cycloalkyl, —$(CH═CH—CH_2—CH_2)$-cycloalkyl, —$(CH_2—CH═CH—CH_2)$-cycloalkyl, —$(CH_2—CH_2—CH═CH)$-cycloalkyl, —$(C(CH_3)═CH—CH_2)$-cycloalkyl, —$(CH═C(CH_3)—CH_2)$-cycloalkyl whereby the term cycloalkyl is defined above.

The term heterocyclyl means e.g. piperidinyl-, morpholinyl-, thiomorpholinyl-, piperazinyl-, tetrahydrofuranyl-, tetrahydrothienyl-, imidazolidinyl- or pyrrolidinyl-whereby the heterocyclyl group may be bound via any possible ring atom. The heterocyclyl group may be substituted by $C_1-C_5$-alkyl (optionally substituted), hydroxy-, $C_1-C_5$-alkoxy-, $NR^4R^5$—, halogen, cyano-, $COOR^8$—, CHO—. If possible these substitutents may also be bound to one of the free nitrogen atoms if any. N-oxides are also included in the definition.

The term heterocyclyl-$(C_1-C_{10})$-alkenyl- means an alkylene group as defined above which is connected to the heterocyclyl group which also is already defined above.

The term heterocyclyl-$(C_2-C_8)$-alkenyl- means an alkylenylene group as defined above which is connected to the heterocyclyl group which also is already defined above.

The term aryl in the sense of the invention means aromatic or partially aromatic carbocyclic rings having 6 to 14 carbon atoms, e.g. phenyl and which may also may have a condensed a second or third ring such as e.g. napthyl or anthranyl. Further examples are phenyl, naphthyl, tetralinyl, anthranyl, benzoxazinone, dihydroindolone, indanyl, and indenyl.

The aryl groups may be substituted at any position leading to a stable molecule by one or several substitutents, e.g. 1-3 substitutents, such as e.g. hydroxy, halogen, $C_1-C_5$-alkyl, $C_1-C_5$-alkoxy, cyano, $CF_3$, nitro, $COO(C_1-C_5$-alkyl or benzyl) or a heteroaryl group, preferably by 1-3 $C_1-C_5$-alkyl groups, hydroxyl, halogen, cyano or $C_1-C_5$-alkoxy.

The optionally substituted phenyl group is one aspect of the invention. Yet another aspect are the compounds of formula I whereby $R^8$ is not phenyl.

The term heteroaryl means an aromatic ring system having 1-3 heteroatoms selected from nitrogen, oxygen or sulfur, for five membered rings the maximum number of heteroatoms is three whereby only two oxygen or sulfur atoms are allowed provided that these two are not directly bound to each other. Possible heteroaryl rings are e.g. thienyl, furanyl, pyrrolyl, oxazolyl, thiazolyl, imidazolyl, pyrazolyl, isoxazolyl, isothiazolyl, oxadiazolyl, triazolyl, thiadiazolyl, benzofuranyl, benzothienyl, benzothiazol, benzoxazolyl, benzimidazolyl, indazolyl, indolyl, isoindolyl, pyridyl, pyridazinyl, pyrimidinyl, pyrazinyl, triazinyl, azaindolizinyl-, benzopyridyl, benzopyridazinyl, benzopyrimidinyl, benzopyrazinyl, benzotriazinyl, quinolyl, isoquinolyl, phthalidyl-, thiophthalidyl, indolonyl-, dihydroindolonyl-, isoindolonyl-, dihydroisoindolonyl-, benzofuranyl- or benzimidazolyl.

The compounds of the present invention can exist in stereoisomeric forms such as enantiomers of diastereoisomers depending on their structure and residues as defined in formula I. In one aspect of the invention therefore all these enantiomers, diastereoisomers or mixtures thereof are encompassed. The isolation of enantiomerically or diastereomerically pure isomers can be done by methods of the state of the art, e.g. using column chromatography with a chiral solid phase.

Should it be possible that the compounds of the invention also exist in tautomeric forms these are also an aspect of the present invention.

In one aspect of the invention all compounds defined in formula I as well as their salts, solvates and solvates of salts are encompassed, especially the salts, solvates and salts of solvates of the compounds disclosed in the examples are one aspect of the invention as long as the disclosed compounds themselves are not already salts, solvates or solvates of the salts.

Salts in the sense of the present invention are not only physiologically unobjectable salts but also salts which might be objectable for pharmaceutical use but which are useful e.g. during the process of isolation or purification.

The term physiologically unobjectable salts includes addition salts of mineral acids, carbonic acids, sulfonic acids, e.g. salts of hydrochloric acid, hydrobromic acid, sulfuric acid, nitric acid, phosphoric acid, methanesulfonic acid, ethanesulfonic acid, toluolsulfonic acid, benzenesulfonic acid, naphthalinesulfonic acid, acetic acid, trifluoroacetic acid, propionic acid, lactic acid, tartaric acid, malic acid, citric acid, fumaric acid, pivalic acid, maleic acid, succinic acid and benzoic acid.

In addition the term physiologically unobjectable salts includes salts of commonly suitable bases, e.g. salts of alkalimetall (e.g. sodium- and potassium salts), alkaline earth salts (e.g. calcium- and magnesium salts) and ammonium salts, derivatized from $NH_3$ or organic amines with 1 to 16 carbon atoms, e.g. ethylamine, diethylamine, triethylamine, ethyldiisopropylamine, monoethanolamine, diethanolamine, triethanolamine, dicyclohexylamine, dimethylaminoethanol, prokaine, dibenzylamine, N-methylmorpholin, arginin, lysin, ethylendiamine and N-methylpiperidin.

Solvates in the sense of the invention are such forms of the compounds of the present combinations which build complexes by coordination of solvent molecules in a liquid or a solid phase. Hydrates are special forms of a solvate wherein water molecules are coordinated.

Salts in the sense of the present invention are not only physiologically unobjectable salts but also salts which might be objectable for pharmaceutical use but which are useful e.g. during the process of isolation or purification.

The compounds can be produced by the two processes that are described below (a-b).

Process a)

step a)

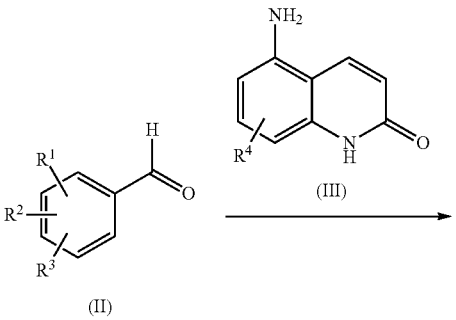

-continued

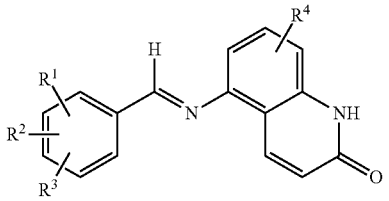

(IV)

Benzaldehydes of type (II) can be condensed with substituted aminoquinolones of type (III) to imines of type (IV) using Lewis acids, preferably titanium alcoholates $Ti(OR)_4$ wherein R is $C_1$-$C_4$-alkyl, such as e.g. tetraethyl orthotitanate or tetra tert. butyl orthotitanate and/or acidic conditions, e.g. organic acids such as acetic acid as reagents. Suitable solvents are e.g. toluene, 1,4-dioxane or mixtures thereof.

Step b)

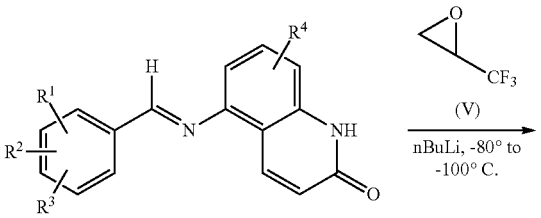

(IV)

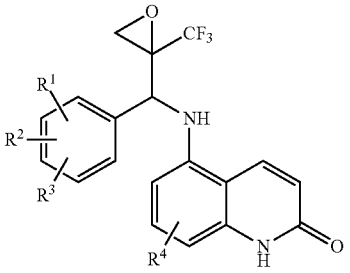

(VI)

Step c)

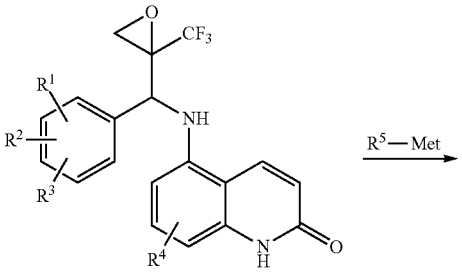

(VI)

-continued

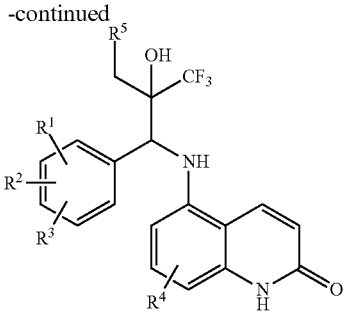

(I)

Imines of type (IV) are treated at low temperatures of −80° to −100° C. with the lithiated epoxide (V) to yield compounds of type (VI). Suitable solvents are e.g. tetrahydrofurane, hexane, diethylether or mixtures thereof. The epoxides (VI) can be opened by nucleophiles of type $R^5$-Met to deliver compound (I). Met means metal and includes alkalimetals e.g. sodium or lithium, alkaline earth metals such as e.g. magnesium, caesium; aluminium, copper, silicon or tin (Sn) which bind the nucleophilic residue $R^5$ of $R^5$-Met depending on their valence and according to the knowledge of a person with ordinary skill. The resulting possible nucleophilic reagents $R^5$-Met are e.g. alkylcuprates, vinylcuprates, thioles, allylsilanes, vinylsilanes, vinylstannanes, grignard compounds whereby $R^5$ is defined as in claim 1, which react in the presence of Lewis acids like e.g. $BF_3$ or $AlMe_3$, $AlCl_3$. Suitable solvents are e.g. diethylether, dimethylformamide, tetrahydrofurane. The epoxides (VI) can also be opened directly by cyanides, amines, alcoholates, thioalcoholates, halogenides and even water or $Cs_2CO_3/H_2O$ in the presence of bases or strong protic acids.

Suitable bases in the sense of the invention are e.g. $Cs_2CO_3$, $K_2CO_3$ or NaOH Suitable strong protic acids are e.g. $HClO_4$, HCl or HBr.

Process b)

step a)

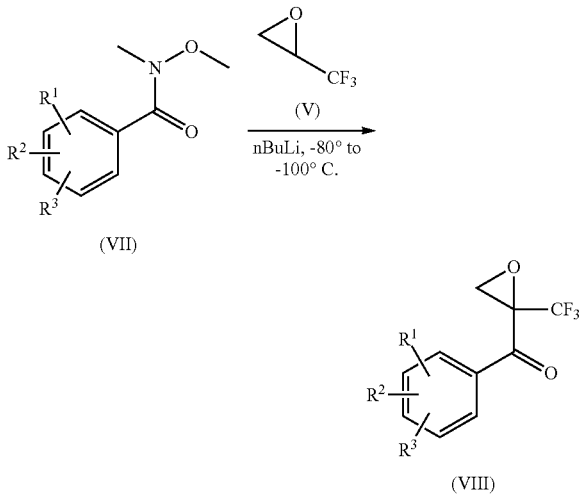

(VII)

(VIII)

Methoxymethylamides of type (VII) are treated at low temperatures of −80° to −100° C. with the lithiated epoxide (V) to yield compounds of type (VIII). Compounds of formula (VII) are commercially available or can be synthesized according to Branca et al, Chimia 49, 10; 1995, 381-385.

step b)

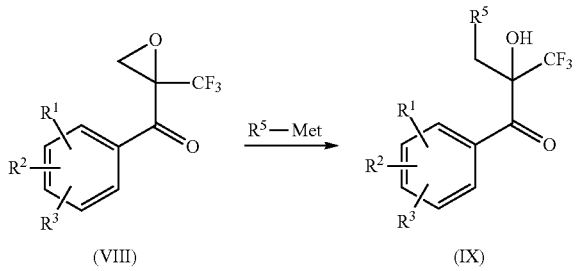

The epoxides (VIII) can be opened by nucleophils of type $R^5$-Met to deliver compound (IX). Possible nucleophiles are alkylcuprates, vinylcuprates, thioles, allylsilanes, vinylsilanes, vinylstannanes, grignard compounds, in the presence of Lewis acids like $BF_3$ or $AlMe_3$, $AlCl_3$, or directly by cyanides, amines, alcohols, thioalcohols, halogenides and water in the presence of bases or strong protic acids.

Step c)

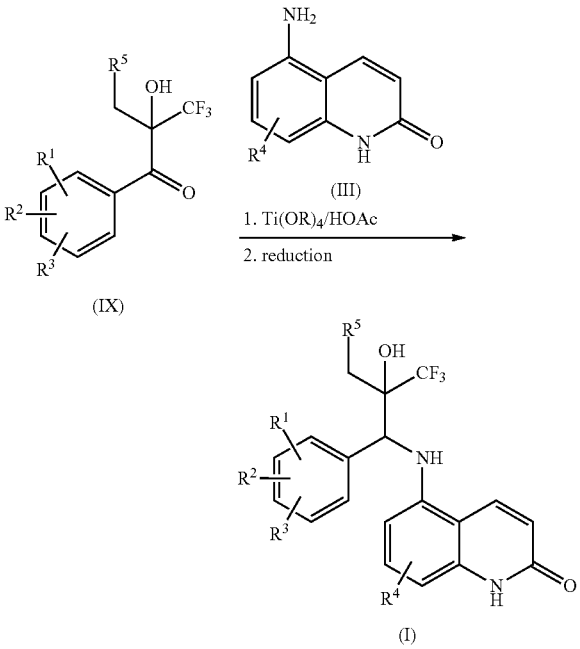

Ketones of type (IX) can be condensed with substituted aminoquinolones of type (III) to imines and subsequently or simultaneously reduced to the aminoalcohol I by a reductive amination using complex hydrides like e.g. $NaBH_4$ or $LiAlH_4$ (Katritzky et al. J. Org. Chem. 1995, 60, 7631-7640) or hydrogen in the presence of catalytic amounts of palladium or platinum or by application of an asymmetric organocatlytic transfer hydrogenation (List et al. Angew. Chem. 2005, 117, 7590-7593).

This processes described above can be performed enantioselectively by use of enantiopure epoxide of formula (V) to yield enantiopure compounds of formula (VI), (VIII), (IX) and (I). The last reductive step of b) can be performed in a diastereoselective manner to yield enantiopure compound I when enantiopure compound IX is used as starting material. Alternatively during the process of the production of the compounds of formula I at different stages purification for obtaining enantiomerically or diastereomerically pure intermediates may be performed e.g. intermediates of formula VI, VIII, IX can be purified at the step when they are obtained or compounds of formula I can be purified to obtain enantiomerically or diastereomerically pure end products after the complete reaction cascade. Examples for methods for obtaining enantiopure (enantiomerically pure) compounds are described below. The separation of optical isomers can be performed by separation of one or more of the intermediates and/or separation of the end products. Usually separation of intermediates and separation of end products are alternatives as long as no racemisation had taken place during the production process.

If the compounds according to the invention are present as racemic mixtures, they can be separated into pure, optically active forms according to the methods of racemate separation that are familiar to one skilled in the art. For example, the racemic mixtures can be separated by chromatography on an even optically active carrier material (CHIRALPAK AD®) into the pure isomers. It is also possible to use chiral auxiliary agents as optically pure acids. For that purpose the free hydroxy group is esterified to yield a racemic compound of general formula I with an optically active acid and to separate the diastereoisomeric esters that are obtained by fractionated crystallization or by chromatography, and to saponify the separated esters in each case to the optically pure isomers. As an optically active acid, for example, mandelic acid, camphorsulfonic acid or tartaric acid can be used.

Thus one aspect of the invention is the process of obtaining compounds of formula I in diastereomerically pure form, optionally using chromatography with columns containing chiral material or using chiral auxiliary agents.

Each of the intermediates of the synthesis of the compounds of formula I are one aspect of the present invention as well as especially their use for the synthesis of the compounds of formula I. A specific aspect of the invention are the concrete intermediates as used for the synthesis of the compounds of the examples, either as racemate or in their enantiomerically (having one chiral center) or diastereomerically (having two chiral centers) pure form.

The binding of the substances to the glucocorticoid receptor (GR) and other steroid hormone receptors (mineral corticoid receptor (MR), progesterone receptor (PR) and androgen receptor (AR)) is examined with the aid of recombinantly produced receptors. Cytosol preparations of Sf9 cells, which had been infected with recombinant baculoviruses, which code for the GR, are used for the binding studies. In comparison to reference substance [$^3$H]-dexamethasone, the substances show a high to very high affinity to GR. $IC_{50}$(GR)=6.8 nM, $IC_{50}$(GR)=5.7 nM and $IC_{50}$(GR) =3.1 nM and $IC_{50}$(GR)=7.1 nM was thus measured for the compound from Examples 1, 4, 5 and 7 respectively.

As an essential, molecular mechanism for the anti-inflammatory action of glucocorticoids, the GR-mediated inhibition of the transcription of cytokines, adhesion molecules, enzymes and other pro-inflammatory factors is considered. This inhibition is produced by an interaction of the GR with other transcription factors, e.g., AP-1 and NF-kappa-B (for a survey, see Cato, A. C. B., and Wade, E., BioEssays 18, 371-378, 1996).

The compounds of general formula I according to the invention inhibit the secretion of cytokine IL-8 into the human monocyte cell line THP-1 that is triggered by lipopolysaccharide (LPS). The concentration of the cytokines was determined in the supernatant by means of commercially available ELISA kits. The compound from Examples 4, 5, 7 and 8 showed an inhibition $IC_{50}$(IL8)=0.61 nmol, $IC_{50}$(IL8)=0.19 nmol, $IC_{50}$(IL8)=0.44 nmol and $IC_{50}$(IL8)=3.1 nmol with efficacies of 97%, 98%, 98% and 80% respectively in comparison with dexamethasone as reference.

The anti-inflammatory action of the compounds of general formula I was tested in the animal experiment by tests in the croton oil-induced inflammation in rats and mice (J. Exp. Med. 1995, 182, 99-108). To this end, croton oil in ethanolic solution was applied topically to the animals' ears. The test substances were also applied topically or systemically at the same time or two hours before the croton oil. After 16-24 hours, the ear weight was measured as a yardstick for inflammatory edema, the peroxidase activity as a yardstick for the invasions of granulocytes, and the elastase activity as a yardstick for the invasion of neutrophilic granulocytes. In this test, the compounds of general formula I inhibit the three above-mentioned inflammation parameters both after topical administration and after systemic administration.

One of the most frequent undesirable actions of a glucocorticoid therapy is the so-called "steroid diabetes" [cf., Hatz, H. J., Glucocorticoide: Immunologische Grundlagen, Pharmakologie and Therapierichtlinien [Glucocorticoids: Immunological Bases, Pharmacology and Therapy Guidelines], Wissenschaftliche Verlagsgesellschaft mbH, Stuttgart, 1998]. The reason for this is the stimulation of gluconeogenesis in the liver by induction of the enzymes responsible in this respect and by free amino acids, which are produced from the degradation of proteins (catabolic action of glucocorticoids). A key enzyme of the catabolic metabolism in the liver is tyrosinamino transferase (TAT). The activity of this enzyme can be determined from liver homogenates by photometry and represents a good measurement of the undesirable metabolic actions of glucocorticoids. To measure the TAT induction, the animals are sacrificed 8 hours after the test substances are administered, the livers are removed, and the TAT activity is measured in the homogenate. In this test, at doses wherein they have an anti-inflammatory action, the compounds of general formula I induce little or no tyrosinamino transferase.

Because of their anti-inflammatory and, in addition, anti-allergic, immunosuppressive and antiproliferative action, the compounds of general formula I according to the invention can be used as medications for treatment or prophylaxis of the following pathologic conditions in mammals and humans: In this case, the term "DISEASE" stands for the following indications:

(i) Lung diseases, which coincide with inflammatory, allergic and/or proliferative processes:
- Chronic, obstructive lung diseases of any origin, primarily bronchial asthma
- Bronchitis of different origins
- Adult respiratory distress syndrome (ARDS), acute respiratory distress syndrome
- Bronchiectases
- All forms of restrictive lung diseases, primarily allergic alveolitis,
- All forms of pulmonary edema, primarily toxic pulmonary edema; e.g., radiogenic pneumonitis
- Sarcoidoses and granulomatoses, especially Boeck's disease (ii) Rheumatic diseases/autoimmune diseases/joint diseases, which coincide with inflammatory, allergic and/or proliferative processes:
- All forms of rheumatic diseases, especially rheumatoid arthritis, acute rheumatic fever, polymyalgia rheumatica, Behçet's disease
- Reactive arthritis
- Inflammatory soft-tissue diseases of other origins
- Arthritic symptoms in the case of degenerative joint diseases (arthroses)
- Traumatic arthritides
- Vitiligo
- Collagenoses of any origin, e.g., systemic lupus erythematodes, sclerodermia, polymyositis, dermatomyositis, Sjögren's syndrome, Still's syndrome, Felty's syndrome
- Sarcoidoses and granulomatoses
- Soft-tissue rheumatism (iii) Allergies or pseudoallergic diseases, which coincide with inflammatory and/or proliferative processes:
- All forms of allergic reactions, e.g., Quincke's edema, hay fever, insect bites, allergic reactions to pharmaceutical agents, blood derivatives, contrast media, etc., anaphylactic shock, urticaria, allergic and irritative contact dermatitis, allergic vascular diseases
- Allergic vasculitis (iv) Vascular inflammations (vasculitides)
- Panarteritis nodosa, temporal arteritis, erythema nodosum
- Polyarteris nodosa
- Wegner's granulomatosis
- Giant-cell arteritis (v) Dermatological diseases, which coincide with inflammatory, allergic and/or proliferative processes:
- Atopic dermatitis (primarily in children)
- All forms of eczema, such as, e.g., atopic eczema (primarily in children)
- Rashes of any origin or dermatoses
- Psoriasis and parapsoriasis groups
- Pityriasis rubra pilaris
- Erythematous diseases, triggered by different noxae, e.g., radiation, chemicals, burns, etc.
- Bullous dermatoses, such as, e.g., autoimmune pemphigus vulgaris, bullous pemphigoid
- Diseases of the lichenoid group,
- Pruritis (e.g., of allergic origin)
- Seborrheal eczema
- Rosacea group
- Erythema exudativum multiforme
- Balanitis
- Vulvitis
- Manifestation of vascular diseases
- Hair loss such as alopecia greata
- Cutaneous lymphoma (vi) Kidney diseases, which coincide with inflammatory, allergic and/or proliferative processes:
- Nephrotic syndrome
- All nephritides, e.g., glomerulonephritis (vii) Liver diseases, which coincide with inflammatory, allergic and/or proliferative processes:
- Acute liver cell decomposition
- Acute hepatitis of different origins, e.g., viral, toxic, pharmaceutical agent-induced
- Chronic aggressive hepatitis and/or chronic intermittent hepatitis (viii) Gastrointestinal diseases, which coincide with inflammatory, allergic and/or proliferative processes:

Regional enteritis (Crohn's disease)
Colitis ulcerosa
Gastritis
Reflux esophagitis
Ulcerative colitis of other origins, e.g., native sprue (ix) Proctologic diseases, which coincide with inflammatory, allergic and/or proliferative processes:
Anal eczema
Fissures
Hemorrhoids
Idiopathic proctitis (x) Eye diseases, which coincide with inflammatory, allergic and/or proliferative processes:
Allergic keratitis, uveitis, iritis
Conjunctivitis
Blepharitis
Optic neuritis
Chorioiditis
Sympathetic ophthalmia (xi) Diseases of the ear-nose-throat area, which coincide with inflammatory, allergic and/or proliferative processes:
Allergic rhinitis, hay fever
Otitis externa, e.g., caused by contact dermatitis, infection, etc.
Otitis media (xii) Neurological diseases, which coincide with inflammatory, allergic and/or proliferative processes:
Cerebral edema, primarily tumor-induced cerebral edema
Multiple sclerosis
Acute encephalomyelitis
Meningitis
Various forms of convulsions, e.g., infantile nodding spasms
Acute spinal cord injury
Stroke (xiii) Blood diseases, which coincide with inflammatory, allergic and/or proliferative processes, such as, e.g.: M. Hodgkins or Non-Hodgkins lymphomas, thrombocythemias, erythrocytoses
Acquired hemolytic anemia
Idiopathic thrombocytopenia (xiv) Tumor diseases, which coincide with inflammatory, allergic and/or proliferative processes, such as, e.g.: carcinomas or sarcomas
Acute lymphatic leukemia
Malignant lymphoma
Lymphogranulomatoses
Lymphosarcoma
Extensive metastases, mainly in breast, bronchial and prostate cancers (xv) Endocrine diseases, which coincide with inflammatory, allergic and/or proliferative processes, such as, e.g.:
Endocrine orbitopathy
Thyreotoxic crisis
De Quervain's thyroiditis
Hashimoto's thyroiditis
Basedow's disease
Granulomatous thyroiditis
Lymphadenoid goiter (xvi) Organ and tissue transplants, graft-versus-host disease (xvii) Severe shock conditions, e.g., anaphylactic shock, systemic inflammatory response syndrome (SIRS)

(xviii) Substitution therapy in:
Innate primary suprarenal insufficiency, e.g., congenital adrenogenital syndrome
Acquired primary suprarenal insufficiency, e.g., Addison's disease, autoimmune adrenalitis, meta-infective tumors, metastases, etc.
Innate secondary suprarenal insufficiency, e.g., congenital hypopituitarism
Acquired secondary suprarenal insufficiency, e.g., meta-infective tumors, etc.

(xix) Emesis, which coincide with inflammatory, allergic and/or proliferative processes:
e.g., in combination with a 5-HT3 antagonist in cytostaticagent-induced vomiting (xx) Pains of inflammatory origins, e.g., lumbago (xxi) Other different stages of disease including diabetes type I (insulin-dependent diabetes), osteoarthritis, Guillain-Barré syndrome, restenoses after percutaneous transluminal angioplasty, Alzheimer's disease, acute and chronic pain, arteriosclerosis, reperfusion injury, congestive heart failure, myocardial infarction, thermal injury, multiple organ injury secondary to trauma, acute purulent meningitis, necrotizing enterocolitis and syndromes associated with hemodialysis, leukopheresis, and granulocyte transfusion.

Moreover, the compounds of general formula I according to the invention can be used for treatment and prophylaxis of additional pathologic conditions that are not mentioned above, for which synthetic glucocorticoids are now used (see in this respect Hatz, H. J., Glucocorticoide: Immunologische Grundlagen, Pharmakologie und Therapierichtlinien, Wissenschaftliche Verlagsgesellschaft mbH, Stuttgart, 1998).

All previously mentioned indications (i) to (xx) are described in more detail in Hatz, H. J., Glucocorticoide: Immunologische Grundlagen, Pharmakologie und Therapierichtlinien, Wissenschaftliche Verlagsgesellschaft mbH, Stuttgart, 1998.

All of the diseases mentioned above do have in common that they are thought to be caused by inflammatory, allergic, immunosuppressive or antiproliferative processes. Thus the invention also relates to methods for treatment of inflammatory, allergic, immunosuppressive or antiproliferative diseases and the use of the compounds of formula I or a pharmaceutically acceptable salt thereof for the manufacture of a medicament for the treatment thereof. One special aspect is the treatment of inflammatory diseases.

The glucocorticoid receptor is known to be involved in the process of inflammation Thus another aspect of the invention is a method of treating a glucocorticoid receptor mediated disease state in a mammal, which comprises administering to a mammal in need of such treatment an effective amount of a compound of formula (I), or a pharmaceutically acceptable salt thereof and the use of a compound or formula (I), or a pharmaceutically acceptable salt thereof, as claimed in claim 1-6, for the manufacture of a medicament for use in the treatment of a glucocorticoid receptor mediated disease state.

Another aspect of the invention are compounds of formula (I), or a pharmaceutically acceptable salt thereof, as claimed in claim 1-6 for use in therapy.

For the therapeutic actions in the above-mentioned pathologic conditions, the suitable dose varies and depends on, for example, the active strength of the compound of general formula I, the host, the type of administration, and the type and severity of the conditions that are to be treated, as well as the use as a prophylactic agent or therapeutic agent.

In addition, the invention provides:

(i) The use of one of the compounds of formula I according to the invention or mixture thereof for the production of a medication for treating a DISEASE;

(ii) A process for treating a DISEASE, said process comprises an administration of an amount of the compound according to the invention, wherein the amount suppresses the disease and wherein the amount of compound is given to a patient who requires such a medication;

(iii) A pharmaceutical composition for treating a DISEASE, said treatment comprises one of the compounds according to the invention or mixture thereof and at least one pharmaceutical adjuvant and/or vehicle.

In general, satisfactory results can be expected in animals when the daily doses comprise a range of 1 μg to 100,000 μg of the compound according to the invention per kg of body weight. In the case of larger mammals, for example the human, a recommended daily dose lies in the range of 1 μg to 100,000 μg per kg of body weight. Preferred is a dose of 10 to 30,000 μg per kg of body weight, and more preferred is a dose of 10 to 10,000 μg per kg of body weight. For example, this dose is suitably administered several times daily. For treating acute shock (e.g., anaphylactic shock), individual doses can be given that are significantly above the above-mentioned doses.

The formulation of the pharmaceutical preparations based on the new compounds is carried out in a way that is known in the art by the active ingredient being processed with the vehicles that are commonly used in galenicals, fillers, substances that influence decomposition, binding agents, moisturizers, lubricants, absorbents, diluents, flavoring correctives, coloring agents, etc., and converted into the desired form of administration. In this case, reference is made to Remington's Pharmaceutical Science, 15$^{th}$ Edition, Mack Publishing Company, East Pennsylvania (1980).

For oral administration, especially tablets, coated tablets, capsules, pills, powders, granulates, lozenges, suspensions, emulsions or solutions are suitable.

For parenteral administration, injection and infusion preparations are possible.

For intra-articular injection, correspondingly prepared crystal suspensions can be used.

For intramuscular injection, aqueous and oily injection solutions or suspensions and corresponding depot preparations can be used.

For rectal administration, the new compounds can be used in the form of suppositories, capsules, solutions (e.g., in the form of enemas) and ointments both for systemic and for local treatment.

For pulmonary administration of the new compounds, the latter can be used in the form of aerosols and inhalants.

For local application to eyes, outer ear channels, middle ears, nasal cavities, and paranasal sinuses, the new compounds can be used as drops, ointments and tinctures in corresponding pharmaceutical preparations.

For topical application, formulations in gels, ointments, fatty ointments, creams, pastes, powders, milk and tinctures are possible. The dosage of the compounds of general formula I should be 0.01%-20% in these preparations to achieve a sufficient pharmacological action.

The invention also comprises the compounds of general formula I according to the invention as therapeutic active ingredients.

In addition, the compounds of general formula I according to the invention are part of the invention as therapeutic active ingredients together with pharmaceutically compatible and acceptable adjuvants and vehicles.

The invention also comprises a pharmaceutical composition that contains one of the pharmaceutically active compounds according to the invention or mixtures thereof or a pharmaceutically compatible salt thereof and a pharmaceutically compatible salt or pharmaceutically compatible adjuvants and vehicles.

The compounds of general formula (I) according to the invention can optionally also be formulated and/or administered in combination with other active ingredients.

The invention therefore also relates to combination therapies or combined compositions, wherein a compound of general formula (I) or a pharmaceutically acceptable salt thereof, or a pharmaceutical composition that contains a compound of general formula (I) or a pharmaceutically acceptable salt thereof, is administered either simultaneously (optionally in the same composition) or in succession together with one or more pharmaceutical agents for treating one of the above-mentioned pathologic conditions. For example, for treatment of rheumatoid arthritis, osteoarthritis, COPD (chronic obstructive lung disease), asthma or allergic rhinitis, a compound of general formula (I) of this invention can be combined with one or more pharmaceutical agents for treating such a condition. When such a combination is administered by inhalation, the pharmaceutical agent that is to be combined can be selected from the following list:

A PDE4 inhibitor including an inhibitor of the PDE4D isoform,

A selective β.sub2.adrenoceptor agonist, such as, for example, metaproterenol, isoproterenol, isoprenaline, albuterol, salbutamol, formoterol, salmeterol, terbutaline, orcipresnaline, bitolterol mesylate, pirbuterol or indacaterol;

A muscarine receptor antagonist (for example, an M1, M2 or M3 antagonist, such as, for example, a more selective M3 antagonist), such as, for example, ipratropium bromide, tiotropium bromide, oxitropium bromide, pirenzepine or telenzepine;

A modulator of the chemokine receptor function (such as, for example, a CCR1 receptor antagonist); or An inhibitor of the p38 kinase function.

For another subject of this invention, such a combination with a compound of general formula (I) or a pharmaceutically acceptable salt thereof is used for treatment of COPD, asthma or allergic rhinitis and can be administered by inhalation or orally in combination with xanthine (such as, for example, aminophylline or thyeophylline), which also can be administered by inhalation or orally.

EXPERIMENTAL PART

The various aspects of the invention described in this application are illustrated by the following examples which are not meant to limit the invention in any way.

Example 1

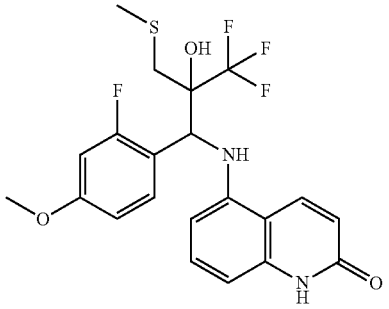

5-{[1-(2-Fluoro-4-methoxyphenyl)-3,3,3-trifluoro-2-hydroxy-2-([methylsulfanyl]methyl)propyl]amino}-1H-quinolin-2-one 5-{[(2-Fluoro-4-methoxyphenyl)(2-trifluoromethyl-oxiranyl)methyl]amino}-1H-quinolin-2-one To 600 mg (3.9 mmol) 5-Amino-7-fluoro-1H-quinolin-2-one and 624 mg (3.9 mmol) 2-fluoro-4-methoxybenzaldehyde in 12 ml toluene are added 18 μacetic acid and 2 g molecular sieve. The mixture is heated over 25 hours under reflux and filtrated through a path of cellites after cooling. The solvent is evaporated and the residue is two times azeotrophed with small portions of toluene to obtain 5-{[1-(2-fluoro-4-methoxyphenyl)-methylidene]amino}-1H-quinolin-2-one are quantitatively. 0.81 ml (11.6 mmol) 1,1,1-trifluoroepoxypropane in 12 ml THF and 3.5 ml hexane are cooled to −100° C. and 3.75 ml of a 2.5 M n-butyl lithium solution (9.4 mmol) in hexane are added over 10 minutes while the temperature does not exceed −95° C. 10 Minutes after complete addition 1.11 g (12 mmol) 5-{[1-(2-fluoro-4-methoxyphenyl)-methylidene]amino}-1H-quinolin-2-one in 10 ml THF are added over 15 minutes while the temperature does not exceed −95° C. After tree hours at −100° C. 3.75 ml diethyl ether are added and the reaction mixture is warmed to −10° C. over one hour. The reaction is quenched by addition of saturated ammonium chloride solution. The phases were separated and the aqueous layer is extracted twice with ethyl acetate, the combined organic phases washed with brine, dried over sodium sulphate and then evaporated. Flash chromatography on silica gel (acetone in hexane 0 to 80%) yields 410 mg of 5-{[(2-Fluoro-4-methoxyphenyl)(2-trifluoromethyl-oxiranyl)methyl]amino}-1H-quinolin-2-one.

$^1$H-NMR ($CDCl_3$); δ=2.59 (dq, 1H), 3.15 (d, 1H), 3.78 (s, 3H), 4.93 (d, 1H), 5.53 (d, 1H), 6.21 (d, 1H), 6.67 (m, 3H), 6.77 (d, 1H), 7.13 (t, 1H), 7.22 (t, 1H), 7.96 (d, 1H).

To 50 mg (0.12 mmol) 5-{[(2-Fluoro-4-methoxyphenyl)(2-trifluoromethyl-oxiranyl)methyl]amino}-1H-quinolin-2-one and 80 mg $Cs_2CO_3$ in 0.5 ml DMF are added 0.18 ml of a 1M solution of methyl mercaptan in DMF. The mixture is stirred vigorously for 4 hours and water is added. The aqueous layer is extracted with ethyl acetate, the organic phases washed with brine and dried over sodium sulphate. After removal of the solvent thin layer chromatography on silica gel (acetone in hexane 50%) yields 27 mg of the title compound.

$^1$H-NMR ($CDCl_3$); δ=2.09 (s, 3H), 2.87 (d, 1H), 3.06 (d, 1H), 3.81 (s, 3H), 5.24 (d, 1H), 5.88 (d, 1H), 6.22 (d, 1H), 6.68 (m, 4H), 7.23 (t, 1H), 7.38 (t. 1H), 7.97 (d, 1H).

Example 2

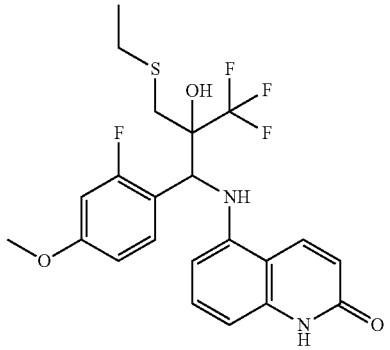

5-{[2-([Ethylsulfanyl]methyl)-1-(2-fluoro-4-methoxyphenyl)-3,3,3-trifluoro-2-hydroxypropyl]amino}-1H-quinolin-2-one To 50 mg (0.12 mmol) 5-{[(2-Fluoro-4-methoxyphenyl)(2-trifluoromethyl-oxiranyl)methyl]amino}-1H-quinolin-2-one and 80 mg $Cs_2CO_3$ in 0.5 ml DMF are added 14 μl (0.18 mmol) of ethyl mercaptan in DMF. The mixture is stirred vigorously for 4 hours and water is added. The aqueous layer is extracted with ethyl acetate, the organic phases washed with brine and dried over sodium sulphate. After removal of the solvent thin layer chromatography on silica gel (acetone in hexane 50%) yields 20 mg of the title compound.

$^1$H-NMR ($CDCl_3$); δ=1.18 (t, 3H), 2.45 (dq, 2H), 2.85 (d, 1H), 3.09 (d, 1H), 3.81 (s, 3H), 5.19 (d, 1H), 5.82 (d, 1H), 6.21 (d, 1H), 6.68 (m, 4H), 7.23 (t, 1H), 7.38 (t, 1H), 7.98 (d, 1H).

Example 3

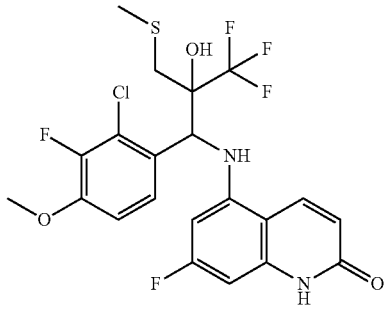

5-{[1-(2-Chloro-3-fluoro-4-methoxyphenyl)-3,3,3-trifluoro-2-hydroxy-2-([methylsulfanyl]methyl)propyl]amino}-1H-quinolin-2-one 2-Chloro-3-fluoro-4-methoxybenzaldehyde 1 g (6.2 mmol) 3-Chloro-2-fluoroanisole in 20 ml THF are cooled to −70° C. and 2.7 ml of a 2.5 M n-butyl lithium solution in hexane are added. After one hour at −70° 3.93 ml DMF in 7 ml THF are added at −70° C. and the mixture is stirred another hour at −70° C. 15 ml of a 1M aqueous HCl are added and the reaction is warmed to ambient temperature over 18 hours. The reaction mixture is partitioned between diethyl ether and water. The aqueous phase is extracted with diethyl ether, the combined organic phases are washed with brine, dried over sodium sulfate and evaporated. The crude product is purified by chromatography on silica gel to yield 0.25 g 2-chloro-3-fluoro-4-methoxybenzaldehyde. $^1$H-NMR ($CDCl_3$); δ=3.98 (s, 3H), 6.98 (dd, 1H), 7.75 (dd, 1H), 10.30 (s, 1H).

5-Amino-7-fluoro-1H-quinolin-2-one

To a solution of 2-bromo-3-fluoroaniline (6.5 g, 34.17 mmol) and pyridine (2.7 g, 34.17 mmol) in 20 ml of $CH_2Cl_2$, cinnamoyl chloride (5.95 g, 35.88 mol) in 10 ml $CH_2Cl_2$ are added dropwise and mixture was refluxed for 30 min. The reaction mixture is diluted with $CH_2Cl_2$, the organic layer washed with diluted HCl, saturated $Na_2CO_3$ solution, water, and dried ($Na_2SO_4$). The solvent is removed in vacuo to give 10.5 g of N-(2-bromo-3-fluorophenyl)-3-phenylacrylamide. To a solution of N-(2-bromo-3-fluorophenyl)-3-phenylacrylamide (10.5 g, 32.8 mmol) in 70 ml of chlor-benzene at 130° C. $AlCl_3$ (21.9 g, 0.164 mol) is added portionwise, the mixture is stirred at this temperature 2 h and poured in ice-water. The precipitate is filtered off and dried. Yield 6.05 g (76%). 6 g (24.8 mmol) of 8-bromo-7-fluoro-1H-quinolin-2-one are refluxed in 30 mL of $POCl_3$ during 2 h, then poured on ice, extracted with benzene. the benzene extract dried ($Na_2SO_4$) to yield 6.1 g 8-bromo-2-chloro-7-fluoroquinoline after solvent removal. To a mixture of 10 ml 10%-oleum and 1.4 g (22.2 mmol) of fuming $HNO_3$ 8-bromo-2-chloro-7-fluoroquinoline (4.8 g 18.5 mmol) is added portionwise. The mixture is heated at 100° C. for 2 h. Additional $HNO_3$ (0.17 g) is added and stirred for additional 1 h. The reaction mixture is poured in ice-water, extracted with EtOAc, filtered through silica gel, and crystallized from heptane-toluene to yield 2.3 g (50%) 8-bromo-2-chloro-7-fluoro-5-nitroquinoline. 2.3 g (7.54 mmol) of 8-bromo-2-chloro-7-fluoro-5-nitroquinoline are heated at 100° C. for 5 h in a solution containing 16 ml of $CH_3COOH$, 3.2 ml of $H_2O$ and 5 ml of conc. HCl. The mixture is poured in water, the formed precipitate is filtered off, stirred in EtOAc and filtered to yield 1.71 g. 8-bromo-7-fluoro-5-nitro-1H-quinolin-2-one. To a suspension 1.7 g (5.92 mmol) of 8-bromo-7-fluoro-5-nitro-1H-quinolin-2-one and 2.3 g (35.5 mmol) of $HCOONH_4$ in 10 ml of ethanol 0.1 g 10% Pd—C are added, and stirred for 2 h at 60° C. A solid disappeared and then formed again. The precipitate is filtered off, dissolved in 3 ml of DMSO and filtered through silica gel. 15 ml of water are added to the eluate, the precipitate is filtered off and dried to yield 0.5 g (47%) 5-Amino-7-fluoro-1H-quinolin-2-one. $^1$H-NMR (DMSO-$d_6$); δ=6.14 (dd, 1H), 6.20 (dd, 1H), 6.23 (d, 1H), 6.27 (br, 2H), 8.06 (d, 1H), 11.50 (br., 1H).

5-{[(2-Chloro-3-fluoro-4-methoxyphenyl)(2-trifluoromethyl-oxiranyl)methyl]amino}-7-fluoro-1H-quinolin-2-one To 1.6 g (9 mmol) 5-amino-7-fluoro-1H-quinolin-2-one and 1.69 g (9 mmol) 2-chloro-3-fluoro-4-methoxybenzaldehyde in 27 ml toluene and 8 ml 1,4-dioxane are added 1.96 ml acetic acid and 7 ml tetrabutyl orthotitanate. The mixture is heated over 20 hours to 110° C., cooled to room temperature and poured into aqueous ammonium fluoride solution. Ethyl acetate is added and the mixture is stirred vigorously for 1 hour. Phases are separated and addition of ethylacetate is repeated two times while stirring is done under reflux and phases are separated while they are still hot. The combined organic phases are concentrated and the residue is purified by flash chromatography on silica gel (ethyl acetate, then methanol in dichloromethane 15% to 20%) to yield 2.17 g of 5-{[1-(2-chloro-3-fluoro-4-methoxyphenyl)methylidene]-amino}-7-fluoro-1H-quinolin-2-one. 465 mg NaH (55% in mineraloil, 9.7 mmol) were washed with dry THF and suspended together with 2.6 g (7.5 mmol) of 5-{[1-(2-chloro-3-fluoro-4-methoxyphenyl)methylidene]amino}-7-fluoro-1H-quinolin-2-one in 90 ml THF. t-Butyldimethylsilyl chloride is added as solid and the mixture is stirred for 3.5 hours while it becomes a clear solution. In parallel 0.96 ml 1,1,1-trifluoro-2,3-epoxypropane in 24 ml THF and 7 ml hexane are cooled to −100° C. and 4.5 ml of a 2.5 M n-butyl lithium solution in hexane are added over 10 minutes while the temperature does not exceed −95° C. 10 Minutes after complete addition the previously prepared 1-{t-butyldimethylsilyl}-5-{[1-(2-chloro-3-fluoro-4-methoxyphenyl) methylidene]amino}-7-fluoroquinolin-2-one solution in THF is added over 30 minutes while the temperature does not exceed −95° C. After 3 hours at −100° C. 7.5 ml diethyl ether are added and the reaction mixture is warmed to room temperature over one hour. The reaction is quenched by addition of saturated ammonium chloride solution. After stirring for 30 minutes the phases are separated and the aqueous layer is extracted with dichloromethan, the combined organic phases are washed with brine, dried over sodium sulphate and then evaporated. Flash chromatography on silica gel (ethyl acetate in hexane 50 to 100%) yields 2.14 g of 5-{[(2-chloro-3-fluoro-4-methoxyphenyl)(2-trifluoromethyloxiranyl)methyl]amino}-7-fluoro-1H-quinolin-2-one which is used for some of the following examples for opening of the oxirane ring with different nucleophiles.

$^1$H-NMR (DMSO-$d_6$); δ=2.62 (m, 1H), 3.29 (d, 1H), 3.87 (s, 3H), 5.49 (d, 1H), 5.83 (d, 1H), 6.34 (d, 1H), 6.37 (d, 1H), 7.04 (d, 1H), 7.22 (dd, 1H), 7.44 (d, 1H), 8.31 (d, 1H), 11.63 (s, 1H).

To 65 mg (0.14 mmol) 5-{[(2-chloro-3-fluoro-4-methoxyphenyl)(2-trifluoromethyl-oxiranyl)methyl] amino}-7-fluoro-1H-quinolin-2-on and 92 mg (0.28 mmol) $Cs_2CO_3$ in 0.5 ml DMF are added 0.21 ml of a 1M solution of methyl mercaptan in DMF. The mixture is stirred vigorously for 20 hours and water is added. The aqueous layer is extracted with ethyl acetate, the organic phases washed with brine and dried over sodium sulphate. After removal of the solvent thin layer chromatography on silica gel (ethyl acetate) yields 22 mg of the title compound.

$^1$H-NMR ($CDCl_3$); δ=1.91 (s, 3H), 2.68 (d, 1H), 3.04 (d, 1H), 3.87 (s, 3H), 5.21 (d, 1H), 5.80 (dd, 1H), 5.94 (d, 1H), 6.38 (dd, 1H), 6.57 (d, 1H), 6.87 (dd, 1H), 7.24 (dd, 1H), 7.84 (d, 1H).

Example 4

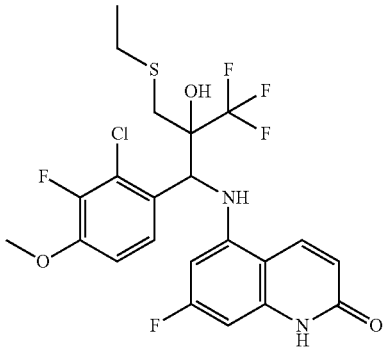

5-{[1-(2-Chloro-3-fluoro-4-methoxyphenyl)-2-([ethylsulfanyl]methyl)-3,3,3-trifluoro-2-hydroxypropyl]amino}-7-fluoro-1H-quinolin-2-one To 66 mg (0.14 mmol) 5-{[(2-chloro-3-fluoro-4-methoxyphenyl)(2-trifluoromethyl-oxiranyl)methyl]amino}-7-fluoro-1H-quinolin-2-on obtained in example 3 and 93 mg (0.29 mmol) $Cs_2CO_3$ in 0.6 ml DMF are added 16 μl (0.22 mmol) of ethyl mercaptan in DMF. The mixture is stirred vigorously for 20 hours and water is added. The aqueous layer is extracted with ethyl acetate, the organic phases washed with brine and dried over sodium sulphate. After removal of the solvent thin layer chromatography on silica gel (ethyl acetate) yields 14 mg of the title compound.

$^1$H-NMR ($CDCl_3$); δ=1.07 (t, 3H), 2.27 (dq, 2H), 2.69 (d, 1H), 3.06 (d, 1H), 3.88 (s, 3H), 5.20 (d, 1H), 5.79 (dd, 1H), 5.92 (d, 1H), 6.37 (dd, 1H), 6.57 (d, 1H), 6.87 (dd, 1H), 7.24 (dd, 1H), 7.84 (d, 1H).

Example 5

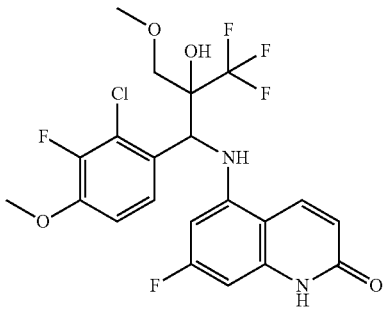

5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one 2.14 g (4.64 mmol) 5-{[(2-chloro-3-fluoro-4-methoxyphenyl)(2-trifluoromethyl-oxiranyl)methyl]amino}-7-fluoro-1H-quinolin-2-on obtained in example 3 are stirred with 2.57 g (7.9 mmol) Caesium carbonate in 37 ml methanol. After 3 days water is added and the aqueous phase is extracted with ethyl acetate. The combined organic phases are washed with brine and dried over sodium sulphate. After removal of the solvent flash chromatography on silica gel (methanol in dichloromethan 0 to 5%) yields 0.98 g of the title compound.

$^1$H-NMR ($CD_3OD$); δ=3.07 (d, 1H), 3.23 (s, 3H), 3.50 (d, 1H), 3.84 (s, 3H), 5.33 (s, 1H), 6.02 (dd, 1H), 6.29 (dd, 1H), 6.43 (d, 1H), 7.05 (dd, 1H), 7.47 (dd, 1H), 8.04 (d, 1H).

Example 6

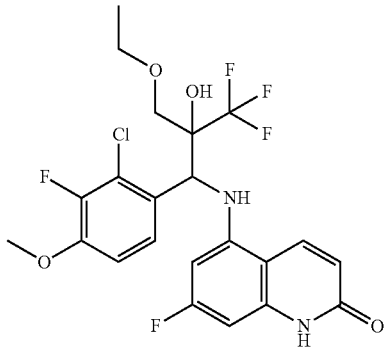

5-{[1-(2-Chloro-3-fluoro-4-methoxyphenyl)-2-(ethoxymethyl)-3,3,3-trifluoro-2-hydroxypropyl]amino}-7-fluoro-1H-quinolin-2-one 70 mg (0.15 mmol) 5-{[(2-chloro-3-fluoro-4-methoxyphenyl)(2-trifluoromethyl-oxiranyl)methyl]amino}-7-fluoro-1H-quinolin-2-on obtained in example 3 are stirred with 84 mg (0.26 mmol) Caesium carbonate in 0.67 ml ethanol. After 40 hours water is added and the aqueous phase is extracted with ethyl acetate. The combined organic phases are washed with brine and dried over sodium sulphate. After removal of the solvent preparative thin layer chromatography on silica gel (ethyl acetate) yields 22 mg of the title compound.

$^1$H-NMR ($CDCl_3$); δ=1.15 (t, 3H), 3.39 (dq, 1H), 3.42 (d, 1H), 3.51 (dq, 1H), 3.69 (d, 1H), 3.87 (s, 3H), 5.26 (d, 1H), 5.86 (dd, 1H), 6.18 (d, 1H), 6.33 (dd, 1H), 6.54 (d, 1H), 6.87 (dd, 1H), 7.25 (dd, 1H), 7.80 (d, 1H).

Example 7

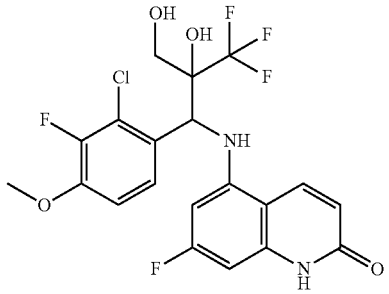

5-{[1-(2-Chloro-3-fluoro-4-methoxyphenyl)-3,3,3-trifluoro-2-hydroxy-2-(hydroxymethyl)-propyl]amino}-7-fluoro-1H-quinolin-2-one 250 mg (0.54 mmol) 5-{[(2-chloro-3-fluoro-4-methoxyphenyl)(2-trifluoromethyl-oxiranyl)methyl]amino}-7-fluoro-1H-quinolin-2-on are stirred with 353 mg (1.1 mmol) Caesium carbonate in 3 ml DMF, 1.9 ml water and 0.5 ml DMSO. Water is added and the aqueous phase is extracted with ethyl acetate. The combined organic phases are washed with brine and dried over sodium sulphate. After removal of the solvent flash chromatography on silica gel (methanol in dichloromethan 0 to 5%) yields 0.98 g of the title compound.

$^1$H-NMR ($CD_3OD$); δ=3.60 (d, 1H), 3.71 (d, 1H), 3.85 (s, 3H), 5.34 (s, 1H), 5.96 (dd, 1H), 6.29 (dd, 1H), 6.45 (d, 1H), 7.06 (dd, 1H), 7.51 (dd, 1H), 8.04 (d, 1H).

Example 8

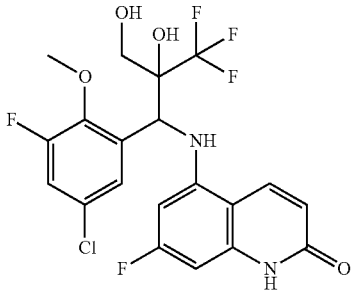

5-{[1-(5-Chloro-3-fluoro-2-methoxyphenyl)-3,3,3-trifluoro-2-hydroxy-2-(hydroxymethyl)-propyl]amino}-7-fluoro-1H-quinolin-2-one 5-Chloro-3-fluoro-2-methoxybenzaldehyde To 5 g (34 mmol) 4-Chloro-2-fluorophenol and 416 mg (3.41 mmol) 4-dimethylaminopyridine in 18 ml THF are added 3.7 ml (37.5 mmol) isopropyl isocyanate and the mixture is heated for 20 hours at 60° C. After cooling down to room temperature 2 M HCl is added and the aqueous phase is extracted with diethyl ether. The combined organic phases are washed with brine, dried over sodium sulfate and evaporated to yield 7.2 g isopropylcarbamic acid 4-chloro-2-fluorophenyl ester as the crude product. To 7.2 g (31 mmol) isopropylcarbamic acid 4-chloro-2-fluorophenyl ester and 5.1 ml tetramethylene diamine in 300 ml diethyl ether are added 5.9 ml (32.5 mmol) (trimethylsilyl)(trifluoromethan)sulfonate at room temperature. After 30 minutes the mixture is cooled to −70° C., 10.2 ml tetramethylene diamine and 27 ml of a 2.5 M n-BuLi solution are added successively. After one hour at −70° 24 ml DMF in are added at −70° C. and the mixture is stirred another hour at −70° C. 130 ml ethanol and 36 ml of a 2 M aqueous NaOH are added and the reaction is warmed to ambient temperature over 18 hours. The reaction mixture is set acidic by addition of 100 ml 2 M aqueous HCl and partitioned between diethyl ether and water. The aqueous phase is extracted with diethyl ether, the combined organic phases are washed with brine, dried over sodium sulphate and evaporated. The crude product is purified by chromatography on silica gel to yield 1.1 g 5-chloro-3-fluoro-2-hydroxybenzaldehyde. 1.1 g (6.1 mmol) 5-chloro-3-fluoro-2-hydroxybenzaldehyde and 1.56 g (11.3 mmol) potassium carbonate are stirred vigorously in 11 ml DMF while 0.7 ml methyliodide are added. Stirring is continued for 18 hours and water is added. The aqueous phase is extracted with diethyl ether, the combined organic phases are dried over sodium sulfate and evaporated. The crude product is purified by chromatography on silica gel (ethyl acetate in hexane 0 to 10%) to yield 570 mg 5-chloro-3-fluoro-2-methoxybenzaldehyde. $^1$H-NMR ($CDCl_3$); δ=4.10 (d, 3H), 7.35 (dd, 1H), 7.59 (m, 1H), 10.35 (s, 1H).

5-{[(5-Chloro-3-fluoro-2-methoxyphenyl)(2-trifluoromethyl-oxiranyl)methyl]amino}-7-fluoro-1H-quinolin-2-one To 0.54 g (3 mmol) 5-amino-7-fluoro-1H-quinolin-2-one and 0.57 g (3 mmol) 5-chloro-3-fluoro-2-methoxybenzaldehyde in 9 ml toluene and 2.6 ml 1,4-dioxane are added 0.65 ml acetic acid and 2.4 ml tetrabutyl orthotitanate. The mixture is heated over 17 hours to 110° C., cooled to room temperature and poured into aqueous ammonium fluoride solution. Ethyl acetate is added and the mixture is stirred vigorously for 1 hour. Phases are separated and addition of ethylacetate is repeated two times while stirring is done under reflux and phases are separated while they are still hot. The combined organic phases are concentrated and the residue is purified by flash chromatography on silica gel (ethyl acetate, then methanol in dichloromethane 10% to 20%) to yield 0.63 g of 5-{[1-(5-chloro-3-fluoro-2-methoxyphenyl)methylidene]-amino}-7-fluoro-1H-quinolin-2-one. 57 mg NaH (55% in mineraloil, 1.4 mmol) were washed with dry THF and suspended together with 0.63 g (1.8 mmol) of 5-{[1-(5-chloro-3-fluoro-2-methoxyphenyl)methylidene]amino}-7-fluoro-1H-quinolin-2-one in 22 ml THF. t-Butyldimethylsilyl chloride is added as solid and the mixture is stirred for 2.5 hours while it becomes a clear solution. In parallel 0.24 ml 1,1,1-trifluoro-2,3-epoxypropane in 6 ml THF and 2 ml hexane are cooled to −100° C. and 1.1 ml of a 2.5 M n-butyl lithium solution in hexane are added over 10 minutes while the temperature does not exceed −95° C. 10 Minutes after complete addition the previously prepared 1-{t-butyldimethylsilyl}-5-{[1-(5-chloro-3-fluoro-2-methoxyphenyl)methylidene]amino}-7-fluoroquinolin-2-one solution in THF is added over 20 minutes while the temperature does not exceed −95° C. After 3.5 hours at −100° C. 2 ml diethyl ether are added and the reaction mixture is warmed to room temperature over one hour. The reaction is quenched by addition of saturated ammonium chloride solution. After stirring for 30 minutes the phases are separated and the aqueous layer is extracted with dichloromethan, the combined organic phases are washed with brine, dried over sodium sulphate and then evaporated. Flash chromatography on silica gel (ethyl acetate in hexane 0 to 100%) yields 152 mg of 5-{[(5-chloro-3-fluoro-2-methoxyphenyl)(2-trifluoromethyloxiranyl)methyl]-amino}-7-fluoro-1H-quinolin-2-one $^1$H-NMR ($CDCl_3$); δ=2.48 (m, 1H), 3.18 (d, 1H), 4.11 (s, 3H), 5.13 (d, 1H), 5.54 (d, 1H), 5.86 (dd, 1H), 6.53 (dd, 1H), 6.64 (d, 1H), 6.94 (m, 1H), 7.14 (d, 1H), 7.88 (d, 1H) and 87 mg of 5-{[1-(5-Chloro-3-fluoro-2-methoxyphenyl)-2-(chloromethyl)-3,3,3-trifluoro-2-hydroxypropyl]amino}-7-fluoro-1H-quinolin-2-one 50 mg (0.11 mmol) 5-{[(5-chloro-3-fluoro-2-methoxyphenyl)(2-trifluoromethyl-oxiranyl)methyl]amino}-7-fluoro-1H-quinolin-2-on are stirred with 67 μl perchloric acid (70%) in 0.55 ml DMF for 24 hours at 40° C. Additional with 67 μl perchloric acid (70%) are added and the mixture is stirred for further 48 hours at 40° C. Saturated aqueous $NH_4Cl$ solution is added and the aqueous phase is extracted with ethyl acetate. The combined organic phases are washed with brine and dried over sodium sulphate. After removal of the solvent thin layer chromatography on silica gel (ethyl acetate) yields 39 mg of the title compound.

$^1$H-NMR ($CD_3OD$); δ=3.49 (d, 1H), 3.78 (d, 1H), 4.14 (d, 3H), 5.48 (s, 1H), 6.12 (dd, 1H), 6.34 (d, 1H), 6.47 (d, 1H), 7.20 (dd, 1H), 7.52 (m, 1H), 8.10 (d, 1H).

Example 9

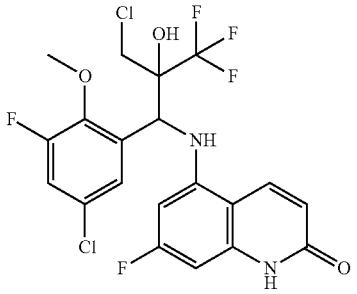

5-{[1-(5-Chloro-3-fluoro-2-methoxyphenyl)-2-(chloromethyl)-3,3,3-trifluoro-2-hydroxypropyl]amino}-7-fluoro-1H-quinolin-2-one Can be isolated as a product in the epoxide synthesis of example 8 after aqueous ammonia chloride work up.

$^1$H-NMR (DMSO-$d_6$); δ=3.88 (d, 1H), 4.00 (d, 3H), 4.19 (d, 1H), 5.49 (d, 1H), 6.12 (d, 1H), 6.37 (d, 2H), 6.51 (d, 1H), 7.42 (d, 1H), 7.66 (s, 1H), 8.24 (d, 1H).

Example 10

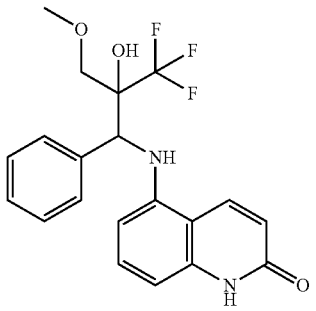

5-{[3,3,3-trifluoro-2-hydroxy-2-([methoxymethyl)-1-phenylpropyl]amino}-1H-quinolin-1-one 3,3,3-trifluoro-2-hydroxy-2-methoxymethypropan-1-one 2.3 ml (26 mmol) 1,1,1-trifluoro-2,3-epoxypropane in 30 ml THF and 8 ml hexane are cooled to −100° C. and 6.3 ml of a 2.5 M n-butyl lithium solution (16 mmol) in hexane are added over 15 minutes while the temperature does not exceed −95° C. 10 Minutes after complete addition 2.0 (12 mmol) g N-methoxy-N-methylbenzamid in 38 ml THF are added over 15 minutes while the temperature does not exceed −95° C. After 5 hours at −100° C. 12 ml diethyl ether are added and the reaction mixture is warmed to room temperature over 14 hours. The reaction is quenched by addition of saturated ammonium chloride solution. The phases were separated and the aqueous layer is extracted twice with ethyl acetate, the combined organic phases washed with brine, dried over sodium sulphate and then evaporated to yield 2.59 g of Phenyl-[2-(trifluoromethyl) oxiranyl]methanone. $^1$H-NMR ($CDCl_3$); δ=3.07 (dq, 1H), 3.38 (d, 1H), 7.50 (t, 2H), 7.65 (tt, 1H), 8.07 (d, 2H).

2.59 g (12 mmol) Phenyl-[2-(trifluoromethyl)oxiranyl] methanone are stirred with 8.8 g (27 mmol) Caesium carbonate in 94 ml methanol. The reaction is quenched by addition of water after 3 days. The aqueous layer is extracted with ethyl acetate, the combined organic phases are washed with brine, dried over sodium sulphate and then evaporated to yield 2.87 g 3,3,3-trifluoro-2-hydroxy-2-methoxymethypropan-1-one. $^1$H-NMR ($CDCl_3$); δ=3.42 (s, 3H), 3.89 (d, 1H), 4.23 (d, 1H), 4.55 (s, 1H), 7.47 (t, 2H), 7.60 (t, 1H), 8.01 (d, 2H).

To 194 mg (1.2 mmol) 5-amino-1H-quinolin-2-one and 300 mg (1.2 mmol) 3,3,3-trifluoro-2-hydroxy-2-methoxymethypropan- 1-one in 4 ml toluene and 1 ml 1,4-dioxane are added 0.26 ml acetic acid and 1 ml tetrabutyl orthotitanate. The mixture is heated over 20 hours to 110° C., cooled to room temperature and poured into aqueous ammonium fluoride solution. Ethyl acetate is added and the mixture is stirred vigorously for 30 minutes. Phases are separated and two times extracted with ethylacetate. The combined organic phases are concentrated to yield quantitatively 5-[(3,3,3-trifluoro-2-hydroxy-2-methoxymethyl-1-phenylpropylidene)amino]-1H-quinolin-2-one. 396 mg (1 mmol) imine in 22 ml methanol is cooled to 5° C. and 700 mg sodium boron hydride are added in multiple portions over the period of 24 hours. The reaction is quenched by addition of saturated ammonium chloride solution and diluted with water and ethyl acetate. The phases are separated, the aqueous layer is extracted with ethyl acetate, the combined organic phases are washed with brine and dried over sodium sulphate. After removal of the solvent flash chromatography on silica gel (ethyl acetate in hexane 0 to 80%) yields 53 mg of the title compound.

$^1$H-NMR ($CD_3OD$); δ=3.45 (s, 3H), 3.47 (d, 1H), 3.64 (d, 1H), 4.97 (s, 1H), 6.19 (d, 1H), 6.58 (t, 2H), 7.16 (t, 1H), 7.30 (m, 3H), 7.50 (d, 2H), 8.05 (d, 1H).

Example 11

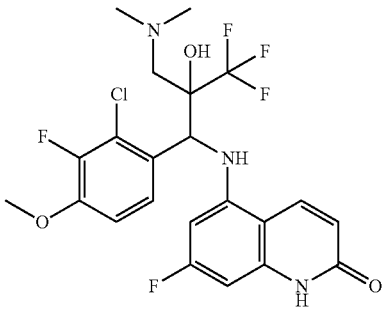

5-{[1-(2-Chloro-3-fluoro-4-methoxyphenyl)-2-(diaminomethyl)-3,3,3-trifluoro-2-hydroxyl)propyl]amino}-7-fluoro-1H-quinolin-2-one 150 mg (0.33 mmol) 5-{[(2-chloro-3-fluoro-4-methoxyphenyl)(2-trifluoromethyl-oxiranyl)methyl]amino}-7-fluoro-1H-quinolin-2-on obtained in example 3 are stirred with 69 mg lithium perchlorate and molecular sieve in 3.25 ml (6.5 mmol) of a 2M THF solution of dimethyamine in a pressure vessel at 60° C. After 20 hors the reaction mixture was filtered from solids which and washed with ethyl acetate. After removal of the solvent flash chromatography on silica gel (ethyl acetate in hexane 0 to 100%) yields 129 mg of the title compound.

$^1$H-NMR ($CDCl_3$); δ=1.68 (br, 3H), 2.30 (d, 1H), 2.36 (br, 3H), 2.77 (br, 1H), 3.87 (s, 3H), 5.09 (d, 1H), 5.81 (d, 1H), 5.98 (d, 1H), 6.35 (d, 1H), 6.56 (d, 1H), 6.88 (dd, 1H), 7.32 (d, 1H), 7.85 (d, 1H).

Example 12

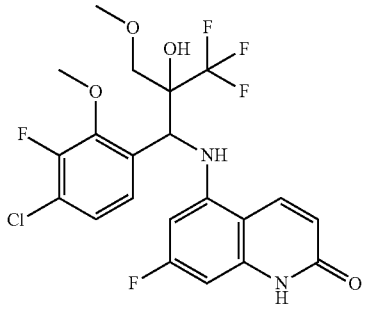

5-{[1-(4-Chloro-3-fluoro-2-methoxyphenyl)-3,3,3-trifluoro-2-hydroxy-2-(methoxymethyl)propyl]amino}-7-fluoro-1H-quinolin-2-one (4-chloro-3-fluoro-2-methoxyphenyl)[2-(trifluoromethyl)oxiranyl]methanone 1 g (6.2 mmol) 3-Chloro-2-fluoroanisole in 10 ml THF are cooled to −70° C. and 2.7 ml of a 2.5 M n-butyl lithium solution in hexane are added. After 1.5 hours at −70° 1 g (6.9 mmol) N,N'-dimethoxy-N,N'-dimethyl urea in 6 ml THF are added at −70° C. and the mixture is stirred another hour at −70° C. 7.5 ml of a 2 M aqueous HCl are added and the reaction is warmed to ambient temperature over 18 hours. The reaction mixture is partitioned between diethyl ether and water. The aqueous phase is extracted with diethyl ether, the combined organic phases are washed with brine, dried over sodium sulfate and evaporated. The crude product is purified by chromatography on silica gel (ethyl acetate in hexane 0 to 30%) to yield 0.59 g 4-chloro-3-fluoro-2, N-dimethoxy-N-methylbenzamid.

$^1$H-NMR ($CDCl_3$); δ=3.35 (br, 3H), 3.49 (br, 3H), 3.98 (s, 3H), 6.99 (dd, 1H), 7.13 (dd, 1H).

0.44 ml (5.1 mmol) 1,1,1-trifluoro-2,3-epoxypropane in 7.5 ml THF and 2.2 ml hexane are cooled to −100° C. and 2.03 ml of a 2.5 M n-butyl lithium solution (5.1 mmol) in hexane are added over 15 minutes while the temperature does not exceed −95° C. 10 minutes after complete addition 0.57 g (2.3 mmol) 4-chloro-3-fluoro-2, N-dimethoxy-N-methylbenzamid in 10 ml THF are added over 15 minutes while the temperature does not exceed −95° C. After 3 hours at −100° C. 2.3 ml diethyl ether is added and the reaction mixture is warmed to room temperature over 14 hours. The reaction is quenched by addition of saturated ammonium chloride solution. The phases were separated and the aqueous layer is extracted twice with diethyl ether, the combined organic phases washed with brine, dried over sodium sulphate and then evaporated to yield 570 mg of (4-chloro-3-fluoro-2-methoxyphenyl)[2-(trifluoromethyl)oxiranyl]methanone.

$^1$H-NMR ($CDCl_3$); δ=2.99 (dq, 1H), 3.37 (d, 1H), 4.14 (d, 3H), 7.18 (m, 1H), 7.19 (m, 1H).

285 mg (0.95 mmol) (4-Chloro-3-fluoro-2-methoxyphenyl)[2-(trifluoromethyl)oxiranyl]methanone are stirred with 622 mg (1.9 mmol) caesium carbonate in 6.7 ml methanol. The reaction is quenched by addition of water after one day. The aqueous layer is extracted with ethyl acetate, the combined organic phases are washed with brine, dried over sodium sulphate and then evaporated to yield 262 mg 1-(4-chloro-3-fluoro-2-methoxyphenyl)-3,3,3-trifluoro-2-hydroxy-2-methoxymethypropan-1-one. To 27 mg (0.15 mmol) 5-Amino-7-fluoro-1H-quinolin-2-one and 50 mg (0.15 mmol) 1-(4-chloro-3-fluoro-2-methoxyphenyl)-3,3,3-trifluoro-2-hydroxy-2-methoxymethypropan-1-one in 0.45 ml toluene and 0.13 ml 1,4-dioxane are added 33 μl acetic acid and 0.12 ml tetra butyl orthotitanate. The mixture is heated over 20 hours to 110° C., cooled to room temperature and poured into aqueous ammonium fluoride solution. Ethyl acetate is added and the mixture is stirred vigorously for 30 minutes. Phases are separated and two times extracted with ethyl acetate. The combined organic phases are concentrated to yield quantitatively 5-{[1-(4-chloro-3-fluoro-2-methoxyphenyl)-3,3,3-trifluoro-2-hydroxy-2-methoxymethylpropylidene]amino}-7-fluoro-1H-quinolin-2-one. The raw imine in 4.2 ml methanol is cooled to 5° C. and 120 mg sodium boron hydride are added in multiple portions over the period of 72 hours. The reaction is quenched by addition of saturated ammonium chloride solution and diluted with water and ethyl acetate. The phases are separated, the aqueous layer is extracted with ethyl acetate, the combined organic phases are washed with brine and dried over sodium sulphate. After removal of the solvent preparative thin layer chromatography on silica gel (acetone in methylene chloride, 30%) yields 9.5 mg of the title compound.

$^1$H-NMR ($CD_3OD$); δ=3.44 (s, 3H), 3.65 (m, 1H), 3.69 (d, 1H), 4.05 (d, 3H), 5.44 (s, 1H), 6.03 (dd, 1H), 6.30 (dd, 1H), 6.45 (d, 1H), 7.12 (dd, 1H), 7.35 (dd, 1H), 7.94 (d, 1H).

Example 13

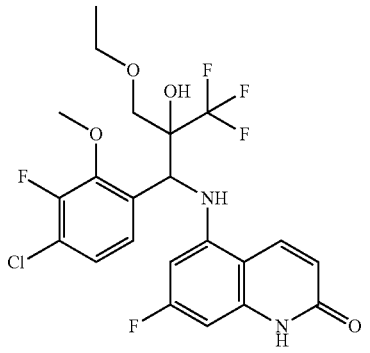

5-{[1-(4-Chloro-3-fluoro-2-methoxyphenyl)-2-(ethoxymethyl)-3,3,3-trifluoro-2-hydroxypropyl]amino}-7-fluoro-1H-quinolin-2-one 1-(4-Chloro-3-fluoro-2-methoxyphenyl)-3,3,3-trifluoro-2-ethoxymethyl-2-hydroxypropan-1-one 285 mg (0.95 mmol) (4-Chloro-3-fluoro-2-methoxyphenyl)-[2-(trifluoromethyl)-oxiranyl]methanone obtained in example 12 are stirred with 622 mg (1.9 mmol) Caesium carbonate in 8 ml ethanol. The reaction is quenched by addition of water after 1 day. The aqueous layer is extracted with ethyl acetate, the combined organic phases are washed with brine, dried over sodium sulphate and then evaporated to yield 173 mg 1-(4-Chloro-3-fluoro-2-methoxyphenyl)-3,3,3-trifluoro-2-ethoxymethyl-2-hydroxy propan-1-one. $^1$H-NMR ($CDCl_3$); δ=1.20 (t, 3H), 3.60 (dq, 1H), 3.62 (dq, 1H), 3.79 (d, 1H), 3.97 (d, 3H), 4.09 (d, 1H), 4.72 (s, 1H), 7.11 (dd, 1H), 7.18 (dd, 1H). To 26 mg (0.15 mmol) 5-Amino-7-fluoro-1H-quinolin-2-one and 50 mg (0.15 mmol) 1-(4-Chloro-3-fluoro-2-methoxyphenyl)-3,3,3-trifluoro-2-ethoxymethyl-2-hydroxy propan-1-one in 0.44 ml toluene and 0.13 ml 1,4-dioxane are added 30 μl acetic acid and 0.11 ml tetrabutyl orthotitanate. The mixture is heated over 20 hours to 110° C., cooled to room temperature and poured into aqueous ammonium fluoride solution. Ethyl acetate is added and the mixture is stirred vigorously for 30 minutes. Phases are separated and two times extracted with ethylacetate. The combined organic phases are concentrated to yield quantitatively 5-{[1-(4-Chloro-3-fluoro-2-methoxyphenyl)-3,3,3-trifluoro-2-ethoxymethyl-2-hydroxypropylidene]amino}-7-fluoro-1H-quinolin-2-one. The raw imine in 4.7 ml methanol is cooled to 5° C. and 180 mg sodium boron hydride are added in multiple portions over the period of 72 hours. The reaction is quenched by addition of saturated ammonium chloride solution and diluted with water and ethyl acetate. The phases are separated, the aqueous layer is extracted with ethyl acetate, the combined organic phases are washed with brine and dried over sodium sulphate. After removal of the solvent preparative thin layer chromatography on silica gel (acetone in methylene chloride 30%) yields 3.2 mg of the title compound.

$^1$H-NMR ($CD_3OD$); δ=1.25 (t, 3H), 3.58 (dq, 1H), 3.59 (dq, 1H), 3.68 (dq, 1H), 3.74 (d, 1H), 4.05 (d, 3H), 5.47 (s, 1H), 6.02 (dd, 1H), 6.30 (dd, 1H), 6.43 (d, 1H), 7.13 (dd, 1H), 7.34 (dd, 1H), 7.93 (d, 1H).

Example 14

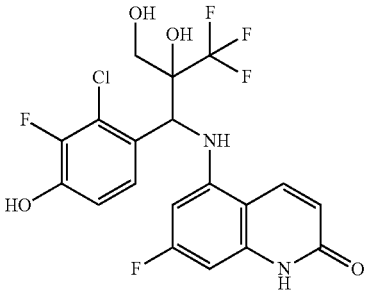

5-{[1-(2-Chloro-3-fluoro-4-hydroxyphenyl)-3,3,3-trifluoro-2-hydroxy-2-(hydroxymethyl)-propyl]amino}-7-fluoro-1H-quinolin-2-one To 100 mg (0.20 mmol) of 5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one of example 5 in 8.6 dichloromethane at −30° C. are added 1.6 ml of a 1M solution of boron tribromide in dichloromethane under argon. The reaction mixture is stirred for 16 hours in a temperature range of between 0° C. and 25° C. The reaction mixture is mixed at 0° C. with saturated sodium bicarbonate solution. After dilution with ethyl acetate the batch is allowed to come to room temperature, stirred for 10 minutes and phases are separated. The aqueous phase is acidified with 4 M HCl and extracted with 10% methanol in dichloromethane. After removal of the solvent preparative thin layer chromatography on silica gel (ethyl acetate/methanol 4:1) yields 16 mg of the title compound.

$^1$H-NMR ($CD_3OD$); δ=3.62 (d, 1H), 3.71 (d, 1H), 5.32 (s, 1H), 5.99 (dd, 1H), 6.30 (dd, 1H), 6.45 (d, 1H), 6.87 (dd, 1H), 7.38 (dd, 1H), 8.05 (d, 1H).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 07076019.4, filed Nov. 22, 2007.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for the treatment of
Atopic dermatitis,
Psoriasis,
Pityriasis rubra pilaris,
Erythematous diseases, triggered by different noxae,
Bullous dermatoses,
Diseases of the lichenoid group,
Pruritis,
Seborrheal eczema,
Rosacea,
Pemphigus vulgaris,
Erythema exudativum multiforme,
Balanitis,
Vulvitis,
Hair loss from alopecia areata,
Cutaneous lymphoma,
Quincke's edema,
insect bites,
allergic reactions to pharmaceutical agents, blood derivatives, or contrast media,
anaphylactic shock,
urticarial,
contact dermatitis, Anal eczema,
Fissures,
Hemorrhoids,
Idiopathic proctitis,
Allergic rhinitis, hay fever,
Otitis externa, or
Otitis media comprising administering to a host in need thereof an effective amount of 5-{[1-(2-Fluoro-4-methoxyphenyl)-3,3,3-trifluoro-2-hydroxy-2-([methylsulfanyl]methyl)propyl]amino}-1H-quinolin-2-one
5-{[2-([Ethylsulfanyl]methyl)-1-(2-fluoro-4-methoxyphenyl)-3,3,3-trifluoro-2-hydroxypropyl]amino}-1H-quinolin-2-one
5-{[1-(2-Chloro-3-fluoro-4-methoxyphenyl)-3,3,3-trifluoro-2-hydroxy-2-([methylsulfanyl]methyl)propyl]amino}-1H-quinolin-2-one
5-{[1-(2-Chloro-3-fluoro-4-methoxyphenyl)-2-([ethylsulfanyl]methyl)-3,3,3-trifluoro-2-hydroxypropyl]amino}-7-fluoro-1H-quinolin-2-one
5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one
5-{[1-(2-Chloro-3-fluoro-4-methoxyphenyl)-2-(ethoxymethyl)-3,3,3-trifluoro-2-hydroxypropyl]amino}-7-fluoro-1H-quinolin-2-one
5-{[1-(2-Chloro-3-fluoro-4-methoxyphenyl)-3,3,3-trifluoro-2-hydroxy-2-(hydroxymethyl)propyl]amino}-7-fluoro-1H-quinolin-2-one
5-{[1-(5-Chloro-3-fluoro-2-methoxyphenyl)-3,3,3-trifluoro-2-hydroxy-2-(hydroxymethyl)-propyl]amino}-7-fluoro-1H-quinolin-2-one
5-{[1-(5-Chloro-3-fluoro-2-methoxyphenyl)-2-(chloromethyl)-3,3,3-trifluoro-2-hydroxypropyl]amino}-7-fluoro-1H-quinolin-2-one
5-{[3,3,3-trifluoro-2-hydroxy-2-([methoxymethyl)-1-phenylpropyl]amino}-1H-quinolin-1-one
5-{[1-(2-Chloro-3-fluoro-4-methoxyphenyl)-2-(diaminomethyl)-3,3,3-trifluoro-2-hydroxypropyl]amino}-7-fluoro-1H-quinolin-2-one
5-{[1-(4-Chloro-3-fluoro-2-methoxyphenyl)-3,3,3-trifluoro-2-hydroxy-2-(methoxymethyl)propyl]amino}-7-fluoro-1H-quinolin-2-one
5-{[1-(2-Chloro-3-fluoro-4-methoxyphenyl)-2-(ethoxymethyl)-3,3,3-trifluoro-2-hydroxypropyl]amino}-7-fluoro-1H-quinolin-2-one
5-{[1-(2-Chloro-3-fluoro-4-hydroxyphenyl)-3,3,3-trifluoro-2-hydroxy-2-(hydroxymethyl)propyl]amino}-7-fluoro-1H-quinolin-2-one or salts, solvates or salts of solvates thereof.

2. The method according to claim 1, wherein compounds, their salts, solvates or salts of solvates are in enantiomerically pure form.

3. The method according to claim 1, comprising administering the enantiomerically pure compounds 5-{(1S,2R)[1-(2-Fluoro-4-methoxyphenyl)-3,3,3-trifluoro-2-hydroxy-2-[([methylsulfanyl]methyl)propyl]amino}-1H-quinolin-2-one
5-{(1S,2R)[2-([Ethylsulfanyl]methyl)-1-(2-fluoro-4-methoxyphenyl)-3,3,3-trifluoro-2-hydroxypropyl]amino}-1H-quinolin-2-one
5-{(1S,2R)[1-(2-Chloro-3-fluoro-4-methoxyphenyl)-3,3,3-trifluoro-2-hydroxy-2-([methylsulfanyl]methyl)propyl]amino}-1H-quinolin-2-one
5-{(1S,2R)[1-(2-Chloro-3-fluoro-4-methoxyphenyl)-2-([ethylsulfanyl]methyl)-3,3,3-trifluoro-2-hydroxypropyl]amino}-7-fluoro-1H-quinolin-2-one
5-{(1S,2S)[1-(2-Chloro-3-fluoro-4-methoxyphenyl)-3,3,3-trifluoro-2-hydroxy-2-(methoxymethyl)propyl]amino}-7-fluoro-1H-quinolin-2-one
5-{(1S,2S)[1-(2-Chloro-3-fluoro-4-methoxyphenyl)-2-(ethoxymethyl)-3,3,3-trifluoro-2-hydroxypropyl]amino}-7-fluoro-1H-quinolin-2-one
5-{(1S,2S)[1-(2-Chloro-3-fluoro-4-methoxyphenyl)-3,3,3-trifluoro-2-hydroxy-2-(hydroxymethyl)propyl]amino}-7-fluoro-1H-quinolin-2-one
5-{(1S,2S)[1-(5-Chloro-3-fluoro-2-methoxyphenyl)-3,3,3-trifluoro-2-hydroxy-2-(hydroxymethyl)propyl]amino}-7-fluoro-1H-quinolin-2-one
5-{(1S,2R)[1-(5-Chloro-3-fluoro-2-methoxyphenyl)-2-(chloromethyl)-3,3,3-trifluoro-2-hydroxypropyl]amino}-7-fluoro-1H-quinolin-2-one
5-{(1S,2S)[3,3,3-trifluoro-2-hydroxy-2-([methoxymethyl)-1-phenylpropyl]amino}-1H-quinolin-1-one
5-{(1S,2R)[[1-(2-Chloro-3-fluoro-4-methoxyphenyl)-2-(diaminomethyl)-3,3,3-trifluoro-2-hydroxypropyl]amino}-7-fluoro-1H-quinolin-2-one
5-{(1S,2S)[1-(2-Chloro-3-fluoro-4-hydroxyphenyl)-3,3,3-trifluoro-2-hydroxy-2-(hydroxymethyl)propyl]amino}-7-fluoro-1H-quinolin-2-one or their salts, solvates or salts of solvates.

4. The method according to claim 1, comprising administering 5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one or a salt, solvate or salt of a solvate thereof.

5. The method according to claim 1, comprising administering 5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one or a salt thereof.

6. The method according to claim 3, comprising administering 5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one or a salt, solvate or salt of a solvate thereof.

7. The method according to claim 3, comprising administering 5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one or a salt thereof.

*8. A method for the treatment of*

*Lung disease due to inflammatory, allergic and/or proliferative processes,*
*rheumatic disease due to inflammatory, allergic and/or proliferative processes,*
*joint diseases due to inflammatory, allergic and/or proliferative processes,*
*autoimmune diseases due to inflammatory, allergic and/or proliferative processes,*
*vascular inflammation,*
*kidney disease due to inflammatory, allergic and/or proliferative processes,*
*liver disease due to inflammatory, allergic and/or proliferative processes,*
*gastrointestinal disease due to inflammatory, allergic and/or proliferative processes,*
*eye diseases due to inflammatory, allergic and/or proliferative processes,*
*neurological disease due to inflammatory, allergic and/or proliferative processes,*
*blood disease due to inflammatory, allergic and/or proliferative processes,*

*tumors due to inflammatory, allergic and/or proliferative processes,*

*endocrine disease due to inflammatory, allergic and/or proliferative processes,*

*graft-versus-host disease in organ and tissue transplants, shock,*

*emesis due to inflammatory, allergic and/or proliferative processes, or*

*Collagenoses,*

*comprising administering to a host in need thereof an effective amount of*

*5-{[1-(2-Fluoro-4-methoxyphenyl)-3,3,3-trifluoro-2-hydroxy-2-([methylsulfanyl]methyl)propyl]amino}-1H-quinolin-2-one*

*5-{[2-([Ethylsulfanyl]methyl)-1-(2-fluoro-4-methoxyphenyl)-3,3,3-trifluoro-2-hydroxypropyl]amino}-1H-quinolin-2-one*

*5-{[1-(2-Chloro-3-fluoro-4-methoxyphenyl)-3,3,3-trifluoro-2-hydroxy-2-([methylsulfanyl]methyl)propyl]amino}-1H-quinolin-2-one*

*5-{[1-(2-Chloro-3-fluoro-4-methoxyphenyl)-2-([ethylsulfanyl]methyl)-3,3,3-trifluoro-2-hydroxypropyl]amino}-7-fluoro-1H-quinolin-2-one*

*5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one*

*5-{[1-(2-Chloro-3-fluoro-4-methoxyphenyl)-2-(ethoxymethyl)-3,3,3-trifluoro-2-hydroxypropyl]amino}-7-fluoro-1H-quinolin-2-one*

*5-{[1-(2-Chloro-3-fluoro-4-methoxyphenyl)-3,3,3-trifluoro-2-hydroxy-2-(hydroxymethyl)propyl]amino}-7-fluoro-1H-quinolin-2-one*

*5-{[1-(5-Chloro-3-fluoro-2-methoxyphenyl)-3,3,3-trifluoro-2-hydroxy-2-(hydroxymethyl)-propyl]amino}-7-fluoro-1H-quinolin-2-one*

*5-{[1-(5-Chloro-3-fluoro-2-methoxyphenyl)-2-(chloromethyl)-3,3,3-trifluoro-2-hydroxypropyl]amino}-7-fluoro-1H-quinolin-2-one*

*5-{[3,3,3-trifluoro-2-hydroxy-2-([methoxymethyl)-1-phenylpropyl]amino}-1H-quinolin-1-one*

*5-{[1-(2-Chloro-3-fluoro-4-methoxyphenyl)-2-(diaminomethyl)-3,3,3-trifluoro-2-hydroxypropyl]amino}-7-fluoro-1H-quinolin-2-one*

*5-{[1-(4-Chloro-3-fluoro-2-methoxyphenyl)-3,3,3-trifluoro-2-hydroxy-2-(methoxymethyl)propyl]amino}-7-fluoro-1H-quinolin-2-one*

*5-{[1-(2-Chloro-3-fluoro-4-methoxyphenyl)-2-(ethoxymethyl)-3,3,3-trifluoro-2-hydroxypropyl]amino}-7-fluoro-1H-quinolin-2-one*

*5-{[1-(2-Chloro-3-fluoro-4-hydroxyphenyl)-3,3,3-trifluoro-2-hydroxy-2-(hydroxymethyl)propyl]amino}-7-fluoro-1H-quinolin-2-one,*

*or salts, solvates or salts of solvates thereof.*

*9. A method according to claim 8, comprising treating*

*chronic, obstructive lung diseases,*

*bronchial asthma,*

*Bronchitis of different origins,*

*Adult respiratory distress syndrome,*

*acute respiratory distress syndrome,*

*Bronchiectases,*

*allergic alveolitis,*

*toxic pulmonary edema,*

*radiogenic pneumonitis,*

*Sarcoidoses,*

*granulomatoses,*

*Boeck's disease,*

*rheumatoid arthritis,*

*acute rheumatic fever,*

*polymyalgia rheumatica,*

*Behçet's disease,*

*Reactive arthritis,*

*arthroses,*

*Traumatic arthritides,*

*Vitiligo,*

*systemic lupus erythematodes,*

*sclerodermia,*

*polymyositis,*

*dermatomyositis,*

*Sjögren's syndrome,*

*Still's syndrome,*

*Felty's syndrome,*

*Sarcoidoses,*

*Soft-tissue rheumatism,*

*Panarteritis nodosa,*

*temporal arteritis,*

*erythema nodosum,*

*Polyarteris nodosa,*

*Wegner's granulomatosis,*

*Giant-cell arteritis,*

*Nephrotic syndrome,*

*nephritides,*

*glomerulonephritis,*

*Acute liver cell decomposition,*

*Acute viral hepatitis,*

*Acute toxic hepatitis,*

*Acute pharmaceutical agent-induced hepatitis,*

*Regional enteritis (Crohn's disease),*

*Colitis ulcerosa,*

*Gastritis,*

*Reflux esophagitis,*

*Ulcerative colitis,*

*Allergic keratitis, uveitis, iritis,*

*Conjunctivitis,*

*Blepharitis,*

*Optic neuritis,*

*Chorioiditis,*

*Sympathetic ophthalmia,*

*Cerebral edema,*

*Multiple sclerosis,*

*Acute encephalomyelitis,*

*Meningitis,*

*convulsions,*

*Acute spinal cord injury,*

*Stroke,*

*M. Hodgkins or Non-Hodgkins lymphoma,*

*thrombocythemias,*

*erythrocytoses,*

*Acquired hemolytic anemia,*

*Idiopathic thrombocytopenia,*

*carcinomas or sarcomas,*

*Acute lymphatic leukemia,*

*Malignant lymphoma,*

*Lymphogranulomatoses,*

*Lymphosarcoma,*

*Extensive metastases,*

*Endocrine orbitopathy,*

*Thyreotoxic crisis,*

*De Quervain's thyroiditis,*

*Hashimoto's thyroiditis,*

*Basedow's disease,*

*Granulomatous thyroiditis or*

*Lymphadenoid goiter.*

*10. A method for substitution therapy in:*

*Innate primary suprarenal insufficiency,*

*Acquired primary suprarenal insufficiency,*

*Innate secondary suprarenal insufficiency, or*

*Acquired secondary suprarenal insufficiency,*

*comprising administering to a host in need thereof an effective amount of*

*5-{[1-(2-Fluoro-4-methoxyphenyl)-3,3,3-trifluoro-2-hydroxy-2-([methylsulfanyl]methyl)propyl]amino}-1H-quinolin-2-one*

*5-{[2([Ethylsulfanyl]methyl)-1-(2-fluoro-4-methoxyphenyl)-3,3,3-trifluoro-2-hydroxypropyl]amino}-1H-quinolin-2-one*

*5-{[1-(2-Chloro-3-fluoro-4-methoxyphenyl)-3,3,3-trifluoro-2-hydroxy-2-([methylsulfanyl]methyl)propyl]amino}-1H-quinolin-2-one*

*5-{[1-(2-Chloro-3-fluoro-4-methoxyphenyl)-2-([ethylsulfanyl]methyl)-3,3,3-trifluoro-2-hydroxypropyl]amino}-7-fluoro-1H-quinolin-2-one*

*5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one*

*5-{[1-(2-Chloro-3-fluoro-4-methoxyphenyl)-2-(ethoxymethyl)-3,3,3-trifluoro-2-hydroxypropyl]amino}-7-fluoro-1H-quinolin-2-one*

*5-{[1-(2-Chloro-3-fluoro-4-methoxyphenyl)-3,3,3-trifluoro-2-hydroxy-2-(hydroxymethyl)propyl]amino}-7-fluoro-1H-quinolin-2-one*

*5-{[1-(5-Chloro-3-fluoro-2-methoxyphenyl)-3,3,3-trifluoro-2-hydroxy-2-(hydroxymethyl)-propyl]amino}-7-fluoro-1H-quinolin-2-one*

*5-{[1-(5-Chloro-3-fluoro-2-methoxyphenyl)-2-(chloromethyl)-3,3,3-trifluoro-2-hydroxypropyl]amino}-7-fluoro-1H-quinolin-2-one*

*5-{[3,3,3-trifluoro-2-hydroxy-2-([methoxymethyl)-1-phenylpropyl]amino}-1H-quinolin-1-one*

*5-{[1-(2-Chloro-3-fluoro-4-methoxyphenyl)-2-(diaminomethyl)-3,3,3-trifluoro-2-hydroxypropyl]amino}-7-fluoro-1H-quinolin-2-one*

*5-{[1-(4-Chloro-3-fluoro-2-methoxyphenyl)-3,3,3-trifluoro-2-hydroxy-2-(methoxymethyl)propyl]amino}-7-fluoro-1H-quinolin-2-one*

*5-{[1-(2-Chloro-3-fluoro-4-methoxyphenyl)-2-(ethoxymethyl)-3,3,3-trifluoro-2-hydroxypropyl]amino}-7-fluoro-1H-quinolin-2-one*

*5-{[1-(2-Chloro-3-fluoro-4-hydroxyphenyl)-3,3,3-trifluoro-2-hydroxy-2-(hydroxymethyl)propyl]amino}-7-fluoro-1H-quinolin-2-one,*

*or salts, solvates or salts of solvates thereof.*

*11. The method according to claim 8, comprising administering 5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one*

*or a salt, solvate or salt of a solvate thereof.*

*12. The method according to claim 8, comprising administering 5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one or a salt thereof.*

*13. The method according to claim 8, comprising administering enantiomerically pure 5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one*

*or a salt, solvate or salt of a solvate thereof.*

*14. The method according to claim 8, comprising administering enantiomerically pure*

*5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one or a salt thereof.*

*15. The method according to claim 9, comprising administering 5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one*

*or a salt, solvate or salt of a solvate thereof.*

*16. The method according to claim 9, comprising administering 5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one or a salt thereof.*

*17. The method according to claim 9, comprising administering enantiomerically pure5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one*

*or a salt, solvate or salt of a solvate thereof.*

*18. The method according to claim 9, comprising administering enantiomerically pure 5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one or a salt thereof.*

*19. The method according to claim 10, comprising administering 5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one*

*or a salt, solvate or salt of a solvate thereof.*

*20. The method according to claim 10, comprising administering 5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one or a salt thereof.*

*21. The method according to claim 10, comprising administering enantiomerically pure 5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one*

*or a salt, solvate or salt of a solvate thereof.*

*22. The method according to claim 10, comprising administering enantiomerically pure 5-{[1-(2-Chloro-3-fluoro-4-methoxyphenyl)-3,3,3-trifluoro-2-hydroxy-2-(methoxymethyl)propyl]amino}-7-fluoro-1H-quinolin-2-one or a salt thereof.*

* * * * *